(12) United States Patent
Phillips et al.

(10) Patent No.: US 11,504,413 B2
(45) Date of Patent: Nov. 22, 2022

(54) MULTI-NUTRIENT COMPOSITION

(71) Applicant: Exerkine Corporation, Hamilton (CA)

(72) Inventors: Stuart Phillips, Hamilton (CA); Gianni Parise, Hamilton (CA); Jennifer Heisz, Hamilton (CA)

(73) Assignee: Exerkine Corporation, Ontario (CA)

(*) Notice: Subject to any disclaimer, the term of this patent is extended or adjusted under 35 U.S.C. 154(b) by 0 days.

(21) Appl. No.: 16/482,891

(22) PCT Filed: Mar. 2, 2018

(86) PCT No.: PCT/CA2018/050249
§ 371 (c)(1),
(2) Date: Aug. 1, 2019

(87) PCT Pub. No.: WO2018/157258
PCT Pub. Date: Sep. 7, 2018

(65) Prior Publication Data
US 2020/0230197 A1    Jul. 23, 2020

Related U.S. Application Data

(60) Provisional application No. 62/466,557, filed on Mar. 3, 2017, provisional application No. 62/609,497, filed on Dec. 22, 2017.

(51) Int. Cl.
*A61K 38/01* (2006.01)
*A23L 33/12* (2016.01)
(Continued)

(52) U.S. Cl.
CPC ............ *A61K 38/018* (2013.01); *A23L 33/12* (2016.08); *A23L 33/155* (2016.08); *A23L 33/16* (2016.08);
(Continued)

(58) Field of Classification Search
None
See application file for complete search history.

(56) References Cited

U.S. PATENT DOCUMENTS

2003/0054026 A1* 3/2003 Blitzer ................ A61K 9/7092
424/449
2007/0154498 A1 7/2007 Bortz et al.
(Continued)

FOREIGN PATENT DOCUMENTS

CA        2246014         1/2000
WO   2004/000297 A1    12/2003

OTHER PUBLICATIONS

Kelly et al. "Nutritional studies on dried functional food ingredients containing omega-3 polyunsaturated fatty acids", Dairy Product Research Center, No. 24, pp. 1-20. (Year: 1999).*
(Continued)

*Primary Examiner* — Isis A Ghali
(74) *Attorney, Agent, or Firm* — Gowling WLG (Canada) LLP

(57) ABSTRACT

A method of improving at least one of the following in an individual: lean mass, muscle strength, cognition, systemic inflammation levels, blood cholesterol levels, blood triglyceride levels and glucose tolerance is provided, comprising administering to the individual a multi-nutrient composition a protein, creatine, vitamin D, calcium and an n-3 fatty acid.

14 Claims, 9 Drawing Sheets

(51) Int. Cl.
| | |
|---|---|
| A23L 33/19 | (2016.01) |
| A23L 33/175 | (2016.01) |
| A23L 33/16 | (2016.01) |
| A23L 33/155 | (2016.01) |
| A61P 3/08 | (2006.01) |
| A61P 3/06 | (2006.01) |
| A61P 25/00 | (2006.01) |
| A61P 29/00 | (2006.01) |
| A61K 31/198 | (2006.01) |
| A61K 31/202 | (2006.01) |
| A61K 31/593 | (2006.01) |
| A61K 33/10 | (2006.01) |

(52) U.S. Cl.
CPC ............. *A23L 33/175* (2016.08); *A23L 33/19* (2016.08); *A61K 31/198* (2013.01); *A61K 31/202* (2013.01); *A61K 31/593* (2013.01); *A61K 33/10* (2013.01); *A61P 3/06* (2018.01); *A61P 3/08* (2018.01); *A61P 25/00* (2018.01); *A61P 29/00* (2018.01); *A23V 2002/00* (2013.01)

(56) References Cited

U.S. PATENT DOCUMENTS

| | | | | |
|---|---|---|---|---|
| 2010/0227007 | A1* | 9/2010 | Romero | A61P 43/00 424/725 |
| 2012/0121726 | A1* | 5/2012 | Giordano | A23L 33/10 424/641 |
| 2012/0195873 | A1 | 8/2012 | Miller et al. | |
| 2012/0220962 | A1* | 8/2012 | Hsu | A61K 9/0014 604/307 |
| 2012/0251512 | A1* | 10/2012 | Farmer | A23K 50/20 424/93.46 |
| 2013/0065824 | A1* | 3/2013 | De Kort | A23L 33/40 514/5.7 |
| 2013/0210780 | A1* | 8/2013 | Jourdan | A61K 31/198 514/167 |
| 2015/0132440 | A1* | 5/2015 | Owoc | A61K 38/06 426/73 |
| 2016/0213728 | A1* | 7/2016 | Tsion | A61K 31/4415 |

OTHER PUBLICATIONS

Walser et al. "Omega-3 fatty acid supplementation enhances stroke volume and cardiac output during dynamic exercise", European Journal Appl. Physiol., 104:455-461. (Year: 2008).*

Silva et al. "Omega-3 supplements for patients in chemotherapy and/or radiotherapy: A systemic review", Clinical nutrition, 1-8. (Year: 2014).*

International Search Report—PCT/CA2018/050249 dated May 28, 2018.

Written Opinion of the International Searching Authority—PCT/CA2018/050249 dated May 28, 2018.

Greenwood et al.—"Nutritional Supplements in Sports & Exercise", 2nd edition, Springer New York, 2015.

Morely et al.—"Nutritional Recommendations for the Management of Sarcopenia", Journal of American Medical Directors Association: 2010; 11 pp. 391-396.

Marzetti et al.—"The Aging Muscle and Sarcopenia: Interaction with Diet and Nutrition", Molecular Basis of Nutrition and Action, New York: Elsevier Inc. 2016; pp. 355-361.

* cited by examiner

MULTI-NUTRIENT COMPOSITION

FIELD OF THE INVENTION

The present invention generally relates to a composition and method for improving the health of an individual, and more particularly relates to a multi-nutrient composition and method for improving at least one of: lean mass, muscle strength, cognition, systemic inflammation levels, blood cholesterol levels, blood triglyceride levels and glucose tolerance in an individual.

BACKGROUND OF THE INVENTION

The health of an individual is generally known to exist in a peak state during young adulthood begins declining during middle adulthood and declines more rapidly during old age. As the global population of older adults steadily increases, more emphasis is being focused on aging in a vigorous, healthful and independent manner. Muscle strength, lean mass, cognition, systemic inflammation levels, blood cholesterol levels, blood triglyceride levels and glucose tolerance are determinants of human health which are generally negatively affected by the aging process. For example, muscle strength and muscle mass have been found to decrease by approximately 1-3% and 0.5-1%, respectively, per year after the age of 30. Furthermore, in a matter of days to weeks, strength and lean mass in older adults can decrease by approximately 10-30% and 5-10%, respectively, during brief periods of muscle disuse (e.g. hospitalization due to acute illness or orthopedic surgery) or injury.

Impairments in muscle strength, lean mass, cognition, systemic inflammation levels, blood cholesterol levels, blood triglyceride levels and glucose tolerance also commonly occur in young adults. For example, conditions such as injury, sedentary lifestyle and poor or inadequate diet may lead to a loss of muscle strength and lean body mass in young adults. Additionally, the obesity epidemic that is characterized by an excessive consumption of energy from dietary intake and lack of daily physical activity is widely known to result in an increase in circulating cholesterol, triglyceride levels, and systemic inflammation, along with a decline in glucose tolerance. Over time, these health impairments can progress to or exacerbate some of the many widespread, chronic diseases such as sarcopenia, obesity, type 2 diabetes, heart disease and dementia.

One of the most effective strategies available for improving health is to participate in a structured program of physical activity, such as endurance or resistance exercise training. Studies conducted over the past several decades have repeatedly shown that exercise or physical activity can improve muscle health, blood lipid levels, systemic inflammation, lean body mass and cognition, however a majority of the population in many developed countries are not active at recommended levels. Primary reasons for which individuals do not engage in exercise include that it is inconvenient, costly, time consuming, difficult to perform, boring or otherwise unenjoyable.

Consuming a healthy, well-balanced diet without excessive proportion size is another well-known way to maintain a state of good health. Similar to exercise, however, there are many barriers to eating a healthy diet, such as a lack of access to, greater cost of, and greater time commitment required to prepare it, as well as the unpalatability of many healthy foods or meals in comparison to less healthy alternatives.

It would be desirable, thus, to provide a convenient nutritional composition and method for improving the health of an individual, such as muscle health, blood lipid levels, systemic inflammation levels, lean body mass and cognition.

SUMMARY OF THE INVENTION

A multi-nutrient composition has now been developed which has been determined to improve at least one of: lean mass, muscle strength, systemic inflammation levels, cognition, blood cholesterol levels, blood triglyceride levels and glucose tolerance in an individual.

Thus, in a first embodiment of the present invention, a multi-nutrient composition comprising a protein source, creatine, vitamin D, calcium and an n-3 fatty acid source is provided.

In another embodiment, a method is provided for improving at least one of the following in an individual: lean mass, muscle strength, cognition, systemic inflammation levels, blood cholesterol levels, blood triglyceride levels and glucose tolerance, comprising administering to the individual a multi-nutrient composition comprised of a protein source, creatine, vitamin D, calcium and an n-3 fatty acid source.

In another embodiment, a method is provided for increasing lean mass, muscle strength, cognition and glucose tolerance, and reducing systemic inflammation levels, blood cholesterol levels and blood triglyceride levels in an individual, comprising administering to the individual a multi-nutrient composition comprising a protein source, creatine, vitamin D, calcium and an n-3 fatty acid source.

In another embodiment, a method is provided for increasing cognition and improving at least one of the following in an individual: lean mass, muscle strength, systemic inflammation levels, blood cholesterol levels, blood triglyceride levels and glucose tolerance, comprising administering to the individual a multi-nutrient composition comprising a protein source, creatine, vitamin D, calcium and an n-3 fatty acid source.

In another embodiment, a method is provided for improving at least one of the following in an individual: lean mass, muscle strength, cognition, systemic inflammation levels, blood cholesterol levels, blood triglyceride levels and glucose tolerance, comprising administering to the individual a multi-nutrient composition comprising a protein source, creatine, vitamin D, calcium and an n-3 fatty acid source, wherein the individual is performing regular exercise.

In another embodiment, a method of improving muscle strength, cognition and systemic inflammation levels, in an individual is provided, comprising administering to the individual a composition comprising a protein source, creatine, vitamin D, calcium and an n-3 fatty acid source, wherein the individual is performing regular exercise.

In a further embodiment, kit is provided comprising a first composition comprising a protein, creatine, vitamin D and calcium, and a second composition comprising an n-3 fatty acid.

These and other aspects of the present invention will become apparent in the detailed description that follows, by reference to the following figures.

DETAILED DESCRIPTION OF THE INVENTION

Figure 1:
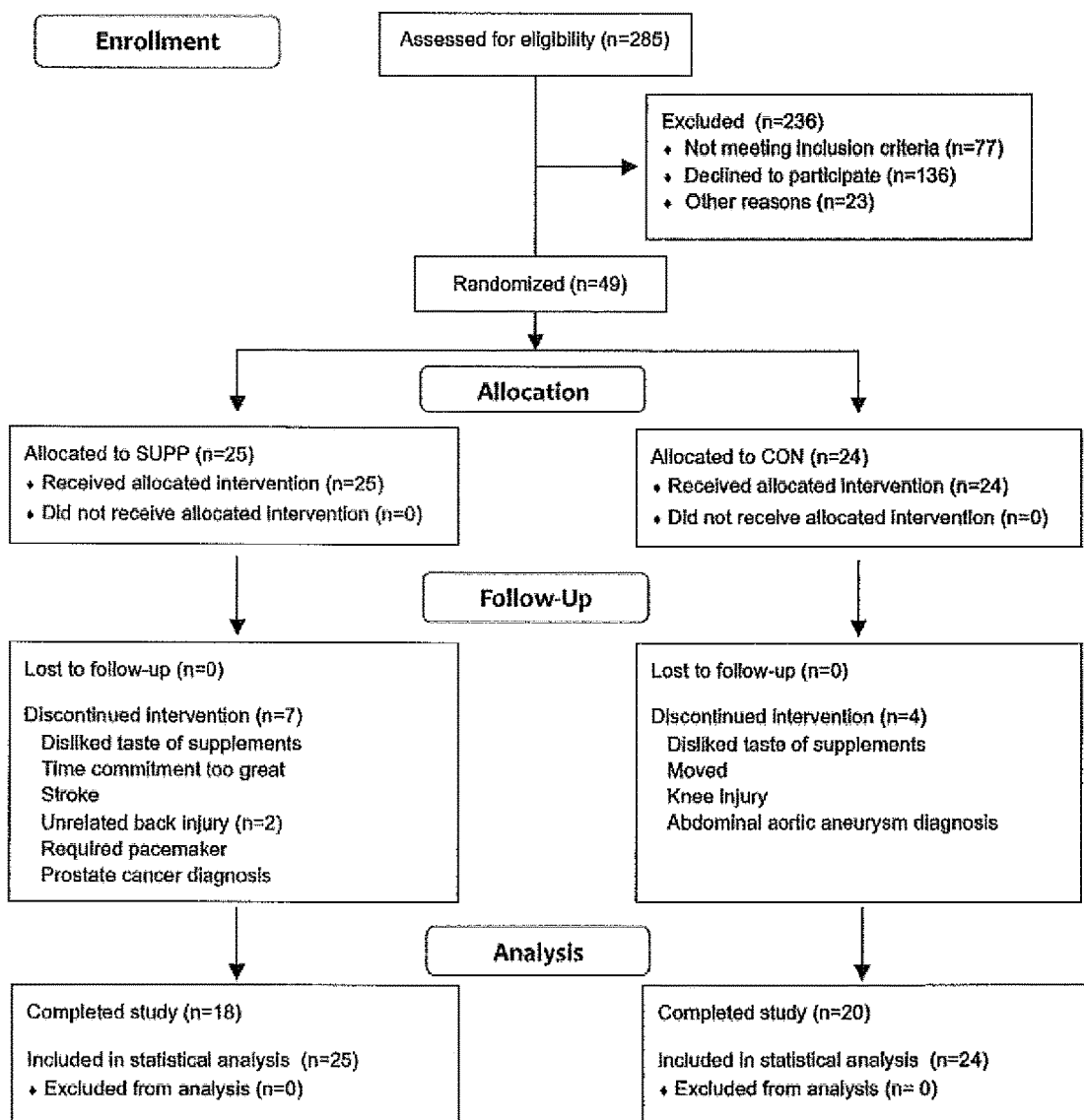
FIG. 1 illustrates a CONSORT flow diagram illustrating the movement of participants through a study protocol from recruitment through to final analysis.

A multi-nutrient composition comprising a protein source, creatine, vitamin D, calcium and an n-3 fatty acid source is provided and is useful to improve aspects of the health of an individual such as muscle strength, lean mass, cognition, systemic inflammation levels, blood cholesterol levels, blood triglyceride levels and glucose tolerance.

The multi-nutrient composition comprises at least one protein source. The protein source may be selected from any suitable protein source, including those from an animal source, a dairy source, a plant source, an insect source or any combination thereof. Non-limiting examples of insect sources of protein include: cricket protein, grasshopper protein, mealworm protein, earthworm protein and any combination thereof. Non-limiting examples of animal sources of protein include: cow protein, pig protein, goat protein, lamb protein, poultry protein (such as chicken, duck, goose, pheasant and the like), wild game protein, seafood protein (such as fish and shellfish) and any combination thereof. Non-limiting examples of dairy sources of protein include: whey protein, whey protein concentrate, whey protein isolate, milk protein concentrate, milk protein isolate, powdered fat-free milk, micellar casein, acid casein, potassium caseinate, calcium caseinate, sodium caseinate and any combination thereof. Non-limiting examples of plant sources of protein include: pea protein, yeast protein, soy protein, corn protein, wheat protein, rice protein, canola protein, peanut protein, bean protein, lentil protein, and any combination thereof. The protein source may be non-hydrolyzed, partially hydrolyzed or hydrolyzed and may be in the form of an intact protein, amino acid or peptide. Non-limiting examples of amino acids may include essential amino acids such as: leucine, isoleucine, valine, tryptophan, methionine, threonine, phenylalanine and lysine and semi-essential amino acids such as: histidine and arginine and non-essential amino acids such as tyrosine, aspartic acid, glycine, alanine, cysteine, arginine, glutamic acid, proline, glutamine, serine, asparagine, taurine and any combination thereof. Preferably, the protein source is a high-quality protein source, at least comprising each of the essential amino acids. Preferably, the protein source is whey protein isolate enriched with leucine which has been found to enhance muscle protein synthesis. In one embodiment, the protein source of the multi-nutrient composition comprises about 1-95% of the dry weight of the multi-nutrient composition, such as from about 20-60%, or from about 30-50% of the dry weight of the composition. In another embodiment, the multi-nutrient composition comprises about 1-80 g of a protein source, for example, up to about 10 g, 20 g, 30 g, 40 g, 50 g, 60 g, 70 g or 80 g. In a particular embodiment, the composition comprises about 15-35 g, such as 28 g. The term "about" is used herein to refer to an amount within 10% or less of the indicated amount, and preferably an amount within 5% or less, wherein the amount is either greater or less than the indicated amount.

Leucine has been determined to combine with a protein source, such as whey protein isolate, to provide a synergistic effect. Thus, a reduced amount of the protein source is required when combined with leucine to yield a given muscle protein synthesis response than the amount of protein required if administered without leucine. Thus, leucine enrichment of a protein may reduce the total amount of protein in the composition by about 10%, 20%, 30%, 40% or more, while still achieving a desirable muscle protein synthesis response. For example, when a suboptimal dose of whey protein isolate (e.g. 6.25 g of whey) is administered in conjunction with 4.25 g of leucine (whey+leu), the muscle protein synthesis response was comparable to that resulting from the administration of 25 g of whey protein (with no added leucine). Thus, in this case, a composition comprising leucine-enriched whey protein totaling only 10.5 g of total protein source yielded a muscle protein synthesis response similar to that achieved with a composition comprising 25 g of whey protein.

The multi-nutrient composition comprises creatine in any suitable form, such as creatine monohydrate, creatine anhydrous, creatine citrate, creatine ethyl ester, creatine nitrate, creatine magnesium chelate, creatine hydrochloride, creatine ascorbate, creatine malate, creatine pyruvate, creatine phosphate, creatine citrate malate, creatine tartrate, creatine HMB (β-hydroxy β-methylbutyrate), effervescent creatine, creatine titrate, buffered creatine, micronized creatine and any combination thereof. Preferably, the creatine is creatine monohydrate. In one embodiment, the creatine of the multi-nutrient composition comprises about 0.1%-40% of the dry weight of the multi-nutrient composition, such as about 1-20%, or about 5-10% of the dry weight of the composition. In another embodiment, the multi-nutrient composition comprises about 0.1-10 g of creatine and preferably, about 1-5 g, such as 2.5 g.

The multi-nutrient composition comprises vitamin D in any suitable form, such as vitamin D2 (ergocalciferol), vitamin D3 (cholecalciferol) and any combination thereof. Preferably, the vitamin D is vitamin D3. In one embodiment, the vitamin D of the multi-nutrient composition comprises about 0.0000004-0.001% of the dry weight of the multi-nutrient composition, such as about 0.00001-0.0005%, or about 0.00005-0.0001% of the dry weight of the composition. In another embodiment, the multi-nutrient composition comprises about 50-4000 IU of vitamin D and preferably, between about 500-3000 IU, such as 1000 IU of vitamin D. For clarity, IU refers to International Units. For vitamin D, 1 μg is 40 IU.

The multi-nutrient composition comprises a source of calcium in any suitable form, such as calcium carbonate, bonemeal calcium, dolomite calcium, calcium citrate, oyster shell calcium, calcium gluconate, calcium lactate, calcium lactobionate, calcium phosphate, calcium citrate malate, calcium orotate, calcium ascorbate, calcium hydroxyapatite, microcrystalline hydroxyapatite and any combination thereof. Preferably, the source of calcium is a calcium salt such as calcium carbonate, or a source of calcium with enhanced bioavailability such as calcium citrate, or a combination thereof. In one embodiment, the multi-nutrient composition comprises a source of calcium in an amount of about 0.1-10% of the dry weight of the multi-nutrient composition, such as about 0.1-5%, or 1-2% of the dry weight of the composition. In another embodiment, the multi-nutrient composition comprises about 10-2000 mg of a calcium source, and preferably between about 100-1000 mg, such as 400 mg of a calcium source.

The multi-nutrient composition comprises at least one n-3 fatty acid. N-3 fatty acids are polyunsaturated fatty acids having a double bond between the third and fourth carbons of the carbon chain. N-3 fatty acids are also commonly referred to as omega-3 fatty acids. Non-limiting examples of n-3 fatty acids include eicosapentaenoic acid (EPA), docosahexaenoic acid (DHA), alpha-linolenic acid (ALA), stearidonic acid, docosapentaenoic acid, and combinations thereof. The n-3 fatty acid may be obtained from any suitable n-3 fatty acid source, including a cold water fish (e.g. cod, salmon, tuna, sardines, mackerel, krill and squid), algae, dark leafy green vegetables, plant and plant seed oils (e.g. flaxseed oil, canola oil and walnut oil), nuts (e.g. walnuts) and any combination thereof. The n-3 fatty acid may be in the triglyceride form typically found in nature, in ethyl ester form or free-fatty acid form, and may be in liquid or powdered form. Preferably, the n-3 fatty acid is a combination of EPA and DHA. In one embodiment, the n-3 fatty acid of the multi-nutrient composition comprises about 0.1%-20% of the dry weight of the multi-nutrient composition, such as about 0.1-10%, or about 1-4% of the dry weight of the composition. In another embodiment, the multi-nutrient composition comprises about 10 mg-5000 mg of an n-3 fatty acid, and preferably, about 200-2000 mg, such as 750 mg.

In one embodiment, the multi-nutrient composition comprises 15-60 g of whey protein isolate, 1-5 g of creatine monohydrate, 500-3000 IU of vitamin D3, 100-1000 mg of calcium carbonate, 100-1200 mg of DHA and 100-1500 mg of EPA. For example, the multi-nutrient composition may comprise 60 g of whey protein isolate, 5 g of creatine monohydrate, 1000 IU of vitamin D3, 800 mg of calcium carbonate, 890 mg of DHA and 1400 mg of EPA.

In another embodiment, the multi-nutrient composition comprises 15-60 g of whey protein isolate, 1-5 g of leucine, 1-5 g of creatine monohydrate, 500-3000 IU of vitamin D3, 100-1000 mg of calcium carbonate or citrate, 100-1200 mg of DHA and 100-1500 mg of EPA. For example, the multi-nutrient composition may comprise 32 g of whey protein isolate, 2 g of leucine, 3 g of creatine monohydrate, 1000 IU of vitamin D3, 800 mg of calcium carbonate or citrate, 800 mg of DHA and 800 mg of EPA.

In another embodiment, the multi-nutrient composition comprises 7-20 g of whey protein isolate, 7-20 g of micellar casein, 1-5 g of leucine, 1-5 g of creatine monohydrate, 500-3000 IU of vitamin D3, 100-1000 mg of calcium carbonate, 100-1200 mg of DHA and 200-1500 mg of EPA. For example, the multi-nutrient composition may comprise 16 g of whey protein isolate, 16 g of micellar casein, 2 g of leucine, 3 g of creatine monohydrate, 1000 IU of vitamin D3, 800 mg of calcium carbonate or citrate, 800 g of DHA and 800 g of EPA.

According to one embodiment, the multi-nutrient composition may be used as a sole, primary, or supplemental source of nutrition. Where the multi-nutrient composition is used as a sole source of nutrition, the composition will generally comprise other essential nutrients required in an adequate diet, such as vitamins, minerals, carbohydrates and fats as would be appreciated by one of skill in the art.

The multi-nutrient composition may be formulated with at least one additional source of nutrition, including, but not limited to, carbohydrates, additional lipids, fibre, vitamins, minerals, antioxidants, prebiotics, probiotics, phytochemicals or phytonutrients.

Carbohydrates suitable for inclusion in the multi-nutrient composition include any food-grade carbohydrate which is suitable for oral administration to an individual. Suitable carbohydrates include the following non-limiting examples: quickly-digestible carbohydrates such as monosaccharides and disaccharides (e.g. glucose, fructose, sucrose, dextrose and maltose), molasses, honey, maple syrup, corn syrup, high fructose corn syrup, sugar alcohols (e.g. xylitol, maltitol, erythritol, sorbitol, hydrogenated starch hydrolysates, isomalt and mannitol) or more slowly-digestible carbohydrates such as katakuri starch, cornstarch, potato starch, arrowroot, alginin, xanthan gum, locust bean gum, oat bran, wheat bran and rice bran, or combinations thereof.

The multi-nutrient composition may comprise any food-grade source of fibre which is suitable for oral administration to an individual. Suitable sources of fibre include the following non-limiting examples: water-soluble dietary fiber such as beta-glucans, pectin, xylose, plant gums, inulin and alginates, and insoluble dietary fiber such as lignin, beta-glucans, xanthan gum, resistant starches and combinations thereof.

The multi-nutrient composition may comprise any food-grade source of additional lipids which is suitable for oral administration to an individual. The term "additional lipids" as used herein is intended to include lipids other than n-3 fatty acids. Suitable sources of additional lipids include the following non-limiting examples: olive oil, safflower oil, canola oil, coconut oil, corn oil, palm oil, palm kernel oil, soybean oil, peanut oil, fish oil, almond oil, sunflower oil, butter, lard, and sources of medium chain triglycerides, long chain triglycerides, monoglycerides, diglycerides and combinations thereof.

The multi-nutrient composition may comprise any food-grade source of vitamins and minerals which are suitable for oral administration to an individual. Suitable vitamins include the following non-limiting examples: vitamin A, vitamin C, vitamin E, vitamin K, thiamine, riboflavin, niacin, pantothenic acid, pyridoxine, folic acid, cobalamin, biotin, carotenoids (e.g. lutein, beta-carotene, lycopene and cryptoxanthin), choline, inositol and combinations thereof, and suitable minerals include, but are not limited to, phosphorus, selenium, chromium, zinc, molybdenum, iodine, chloride, phosphorus, manganese, fluoride, potassium, iron, copper, magnesium, sodium and combinations thereof.

The multi-nutrient composition may comprise any food-grade source of antioxidants which are suitable for oral administration to an individual. Suitable antioxidants include the following non-limiting examples: coenzyme Q10, vitamin A, vitamin E, vitamin C, folic acid, alpha lipoic acid, and beta-carotene, iron, copper, butylated hydroxyamisole, butylated hydroxytoluene, propyl gallate, tertiary butylhydroquinone, resveratrol, and plant phytonutrients or phytochemicals (e.g. flavonoids and lignin). Herbs or herbal extracts (e.g. oregano, Goji berry, dill, garden thyme, rosemary and peppermint), forskolin, tea leaves or tea leaf extracts (e.g. *Camellia sinensis*), coffee bean extracts (e.g. *Coffea canephora* and *Coffea arabica*), brewed coffee or tea or brewed coffee or tea extracts (e.g. green tea, black tea, oolong tea and coffee robusta) and other plants or plant extracts (e.g. beet root) may also be used as a source of antioxidants, as well as combinations of any of the antioxidants.

The multi-nutrient composition may comprise any food-grade source of prebiotics which are suitable for oral administration to an individual. Suitable prebiotics include the following non-limiting examples: dietary fibers and carbohydrate polymers such as cellulose, inulin, gums, trans-galactooligosaccharide, fructans, resistant starches, xylooligosaccharides, hemicelluloses, pectin, sugar alcohols, beta-glucans and combinations thereof.

The multi-nutrient composition may comprise any food-grade source of probiotics which are suitable for oral administration to an individual. Suitable probiotics include the following non-limiting examples: *Lactobacillus Acidophilus, Lactobacillus Reuteri, Lactobacillus Rhamnosus, Lactobacillus Gasseri, Lactobacillus Salivarius, Lactobacillus Bulgaricus, Lactobacillus Helventicus, Lactobacillus Silivarus, Lactobacillus Plantarum, Lactobacillus Casei, Lactobacillus Paracassei, Lactobacillus Fermentum, Bifidobacterium Breve, Bifidobacterium Lactis, Bifidobacterium Longum, Bifidobacterium Bifidum, Bifidobacterium infantis, Bifidobacterium Bifidum, Bacillus Coagulans, Saccharomyces Boulardii, Pediococcus Acidlacti* and combinations thereof.

The multi-nutrient composition may comprise any food-grade source of phytochemicals or phytonutrients which are suitable for oral administration to an individual. Suitable phytochemicals or phytonutrients include the following non-limiting examples: phytosterols including sterols (e.g. cempesterol) and stanol (e.g. sitostanol), soy flavonoids (e.g. genistein and glycitein), garlic and organosulfur compounds (e.g. L-cysteine sulfoxides and γ-glutamyl-L-cysteine peptides), carotenoids (e.g. zeaxanthin alpha-carotene, beta-carotene, lycopene, beta-cryptoxanthin and lutein), resveratrol, curcumin, fiber (e.g. lignin and cellulose), indole 3-carbinol and condensation products (e.g. 3,3'-diindolylmethane and 5,11-dihydroindolo-[3,2-b]carbazole), chlorophyll and chlorophyllin isothiocyanates, isothiocyanates (e.g. sulforaphane and benzyl isothiocyanate) and combinations thereof.

In one embodiment, at least one physiologically acceptable excipient may be included in the multi-nutrient composition. The term "physiologically acceptable" is used herein to refer to excipients which are food-grade and thus, acceptable for consumption or administration to an individual. Examples of suitable excipients, which are not to be construed as limiting, include flavouring agents, sweetening agents, anti-caking agents/flowing agents, emulsifiers, stabilizers, masking agents, colorants, preservatives, disintegrants, binders, thickeners and pH adjusters.

Non-limiting examples of flavouring agents include natural or artificial flavours such as fruit flavours (e.g. raspberry, orange, apple, pomegranate, mixed berry, lemon, lime, watermelon, strawberry, blueberry, pineapple, coconut, grape, cherry, banana, peach, mango, kiwifruit, cranberry), sodium sources (e.g. sodium chloride and monosodium glutamate), high fructose corn syrup, vanilla, chocolate, unsweetened chocolate, honey, molasses, brown sugar, coffee, cocoa, mint, maple, almond, or extracts or combinations thereof. Savoury flavourings may also be used (e.g. beef, chicken or vegetable flavourings).

Non-limiting examples of sweetening agents include natural sweeteners such as, glucose, fructose, sucrose, dextrose, maltose, brown sugar, molasses, honey, maple syrup, corn syrup, high fructose corn syrup, erythritol, xylitol, sorbitol, isomalt, monatin, monellin, curculin, brazzein, tagatose and mannitol, and artificial sweeteners such as aspartame, acesulfame K, saccharin cyclamate and sucralose.

Non-limiting examples of anti-caking agents/flowing agents include silicates and calcium or magnesium stearates.

Non-limiting examples of emulsifiers include agar, gums, egg yoke, lecithin, monostearate, monosodium phosphate, monoglycerides, diglycerides and alginates.

Non-limiting examples of stabilizers include glycerine, agar, gums, alginates and pectin.

Non-limiting examples of masking agents include glycerine, sodium chloride, peppermint, lemon-lime, mint, cherry, black liquorice, peach, apricot, raspberry, or sweetening agents such as aspartame or sucrose.

Non-limiting examples of colorants include those which are suitable for inclusion in foods. For example, commonly used colorants include FD&C blue #1, FD&C blue #2, FD&C citrus red #2, FD&C green #3, FD&C red #3, FD&C red #40, FD&C yellow #5 and FD&C yellow #6.

Non-limiting examples of preservatives include butylated hydroxyanisole, butylated hydroxytoluene, ethylenediaminetetraacetic acid, nitrates (e.g. sodium nitrate), sulfites (sodium bisulfite), benzoates (sodium benzoate), sorbates (e.g. sodium sorbate) and sodium chloride.

Non-limiting examples of disintegrants include starches (e.g. potato starch), alginic acid, cellulose and derivatives thereof, and calcium silicate.

Non-limiting examples of binders include stearic acid, gelatin, saccharides and derivatives thereof, sugar alcohols, polyethylene glycol and cellulose.

Non-limiting examples of thickeners include polysaccharide-based thickeners such as vegetable gums, pectin and starches or protein-based thickeners such as gelatin, egg white and collagen.

Non-limiting examples of pH adjusters include citric acid, ammonium carbonate, ammonium phosphate, calcium carbonate, sodium hydroxide, malic acid and phosphoric acid.

As will be appreciated by one of skill in the art, for each type of excipient (e.g. flavouring agent, sweetener, emulsifier, preservative, etc.), a single excipient may be used, or a combination of two or more may be used.

In one embodiment, the multi-nutrient composition may be formulated for oral administration including, for example, in solid, semi-solid, liquid, semi-liquid, powder, suspension, emulsion, solution, ready-to-drink beverage, gel, bar, pill, tablet or capsule form. The term "oral" or "orally" as used herein is intended to include any method in which the multi-nutrient composition is introduced into the digestive tract including the stomach and small intestine. Examples of oral administration may include administration via mouth, directly into the stomach using a feeding tube, through the nose to the stomach via a feeding tube and through the nose to the small intestine via a feeding tube. In a preferred embodiment, the multi-nutrient composition is provided as a powder or a bar. The powdered composition may be reconstituted in water or any suitable liquid immediately prior to consumption. When provided in powdered form, the multi-nutrient composition may be packaged in individual use containers, packets or sachets, or in larger bulk containers.

The multi-nutrient composition may also be formulated for administration parenterally, and may be combined with at least one pharmaceutically acceptable adjuvant. The expression "pharmaceutically acceptable" means acceptable for use in the pharmaceutical and veterinary arts, i.e. not being unacceptably toxic or otherwise unsuitable. Examples of pharmaceutically acceptable adjuvants include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the composition is formulated for administration by infusion, or by injection either subcutaneously or intravenously. The composition may be prepared as an aqueous solution in sterile and pyrogen-free form and optionally buffered or made isotonic. Thus, the composition may be administered in distilled water or, more desirably, in saline, phosphate-buffered saline or 5% dextrose solution. The composition may also be formulated for topical administration. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered for example, anti-microbial agents may be added to the composition to prevent microbial growth over prolonged storage periods. The composition may include a coating or may be encased in a protective material to prevent undesirable degradation thereof by enzymes, acids or by other conditions that may affect the therapeutic activity thereof.

The multi-nutrient composition may be administered in an effective amount to an individual in need thereof, one or more times per day, for a period ranging from one day to chronic or long-term administration. The term "effective amount" as used herein, refers to an amount which achieves the effects desired by the individual, without surpassing any amount which may cause undesirable side effects. For example, an effective amount of the multi-nutrient composition may be administered 1, 2, 3, 4, 5, 6 or more times per day, or an effective amount of the multi-nutrient composition may be divided into 2, 3, 4, 5, 6 or more servings to be administered throughout the day. In one embodiment, the multi-nutrient composition is administered to an individual in the morning when first waking up. The multi-nutrient composition may also be administered to an individual in the morning and then administered again prior to the individual retiring to bed. The multi-nutrient composition may be administered to an individual in need thereof for 1, 2, 3, 4, 5, 6 or 7 days in a week and for 1, 2, 3, 4, 5, 6, 7, 8, 9, 10 or more weeks. In one embodiment, the multi-nutrient composition is administered chronically to an individual in need thereof. The term "chronically" as used herein refers to the administration of the multi-nutrient composition for a period of at least 2-4 or more months, for example, administration of the multi-nutrient composition on a continual basis beyond 6 months, at a frequency of at least 2 days/week, and preferably at least 3 or more days a week.

The components of the composition may be administered in conjunction, either together, in a single composition, or individually, at the same time or at different times. For example, the protein source, creatine, vitamin D and calcium may be administered together as a powder, while the n-3 fatty acid source may be administered separately as an oil once during the day at the same time as the powder is administered, or at a different time, and at the same frequency or at different frequencies. For example, the powder may be administered twice daily, while the oil is administered once a day.

Accordingly, in a further aspect of the invention, a kit is provided comprising a first component comprising a protein, creatine, vitamin D and calcium, and a second component comprising an n-3 fatty acid. The first component may be in the form of a powder provided in bulk form or as individual doses, e.g. in packets, sachets or capsules, and the second component may be in the form of an oil in bulk form or as individual doses, e.g. in capsules.

The present multi-nutrient composition is useful in a method to improve at least one of the following in an individual: lean mass, muscle strength, cognition, systemic inflammation levels, blood cholesterol levels, blood triglyceride levels and glucose tolerance. The term "individual" is used herein to refer to a mammal, preferably a human. The method comprises administering to the individual an effective amount of the multi-nutrient composition. The term "improve" is used herein with respect to the variables of lean mass, muscle strength, cognition, systemic inflammation levels, blood cholesterol levels, blood triglyceride levels and glucose tolerance to refer to either a healthy increase or a healthy decrease in the variable, i.e. an increase or decrease in the variable that is considered to promote health. Any individual may be treated using the present method, including individuals of any age. The present method is useful for healthy individuals, as well as individuals that require improvement of one or more of lean mass, muscle strength, cognition, systemic inflammation levels, blood cholesterol levels, blood triglyceride levels and glucose tolerance, for example, elderly individuals, bed-ridden individuals, hospitalized individuals and individuals afflicted with a disease or condition that adversely effects one or more of lean mass, muscle strength, cognition, systemic inflammation levels, blood cholesterol levels, blood triglyceride levels and glucose tolerance.

As used herein, the term "muscle" refers to skeletal muscles and non-skeletal muscles which may be consciously controlled such as the diaphragm muscles. The term "muscle strength" as used herein, refers to the amount of force which may be generated by a muscle or group of muscles. Muscle strength may be measured by numerous methods, such as a 1-repetition max (1-RM) test, a grip strength test or callisthenic-type exercise tests (e.g. push-ups). Improved muscle strength refers to an increase in the amount of muscle strength in an individual by at least about 0.5%, and preferably an increase of about 1% or more, e.g. by 5%, 10%, 30%, 50%, 70% or greater from the muscle strength of the individual prior to treatment with the present composition, or at least a reduction in the rate of muscle strength loss in an individual who is losing muscle strength by at least about 1% or more, and preferably a reduction in the rate of muscle strength loss by about 5% or more, e.g. by 10%, 30%, 50%, 70%, 90% or greater from the rate of muscle strength loss in the individual prior to treatment with the present composition.

As used herein, the term "lean mass" refers to the fat-free and bone-free mass of an individual (i.e. the total body mass of an individual, minus the mass contributed by fat tissue and bone tissue). Lean mass may be measured as whole body lean mass, or the lean mass of specific regions of the body such as appendicular lean mass, lower body lean mass or upper body lean mass using X-ray technology, e.g. dual energy X-ray absorptiometry (DEXA). Improved lean mass refers to an increase in the amount of lean mass in an individual by at least about 0.5%, and preferably an increase of about 1% or more, e.g. by 5%, 10%, 30%, 50%, 70% or greater to the lean mass of the individual prior to treatment with the present composition, or a reduction in the rate of lean mass loss by at least about 1% or more, and preferably a reduction of the rate of lean mass loss by about 5% or more, e.g. by 10%, 30%, 50%, 70%, 90% or greater of the rate of lean mass loss of the individual prior to treatment with the present composition.

As used herein, the term "cognition" refers to the cognitive abilities of an individual, which are generally understood to include the mental action or process of acquiring knowledge and understanding through thought, experience, and the senses. Cognition is commonly measured by evaluating three of the primary aspects of cognition: memory, executive functions, and processing speed. The term "memory" as used herein refers to the mental capacity for storing and retrieving information. The term "executive function" as used herein refers to a set of cognitive abilities that regulate cognitive control of behavior. The term "processing speed" as used herein refers to the time in which it takes an individual to perform a mental task. There are numerous methods for measuring cognition, which generally emphasize a particular aspect(s) of cognition to a greater extent than others. For example, common tests of memory include the high-interference memory tasks such as the Kirwan and Stark's Mnemonic Similarity Task and the Rey Auditory Verbal Learning Test (RAVLT). The RAVLT involves recalling two distinct sets of words over a course of time and is thought to evaluate several aspects of memory, including verbal episodic memory, immediate and delayed memory, rate of learning, and susceptibility to memory interference. Common tests to measure executive function include the Go-No-Go task, the Stroop task, the Eriksen Flanker task, The Backwards Digit Span task and the Wisconsin Card Sorting task. Processing speed is commonly evaluated using the Simple Reaction Time task which requires the individual to respond as quickly as possible to a stimulus. The Montreal Cognitive Assessment (MoCA) is a relatively broad test of cognition, which includes measures of memory, executive function and processing speed. Improved cognition refers to an increase in the cognitive ability of an individual by at least about 0.5%, and preferably an increase of about 1% or more, e.g, by 5%, 10%, 30%, 50%, 70% or greater of an aspect of cognition of the individual prior to treatment with the present composition, or at least a reduction in the rate of cognition loss by at least about 1% or more, and preferably a reduction of the rate of cognition loss by about 5% or more, e.g. by 10%, 30%, 50%, 70%, 90% or greater of the rate of cognition loss of the individual prior to treatment with the present composition.

As used herein, the term "systemic inflammation level" refers to the amount of inflammation present in circulation and within tissues of the body. While acute inflammation in response to injurious events is thought to be beneficial, the presence of a chronic-low grade inflammation level is generally thought to be deleterious and likely related to the development of chronic disease such as atherosclerosis, arthritis, insulin resistance and numerous others. Systemic inflammation level is most commonly evaluated by measuring the levels of pro-inflammatory markers such as C-reactive protein (CRP), interleukin-6 (IL-6) and tumor necrosis factor-alpha (TNF-alpha) in circulation. Another common test for evaluating systemic inflammation is to measure the amount of n-3 fatty acids present in the blood of an individual or to compare the amount of n-3 fatty acids to n-6 fatty acids in the blood, since n-3 fatty acids are generally thought to be anti-inflammatory and n-6 fatty acids are generally thought to be pro-inflammatory. Improved systemic inflammation level is a reduction in the markers of systemic inflammation in an individual by at least about 0.5%, and preferably a reduction of about 1% or more, e.g. by 5%, 10%, 30%, 50%, 70% or greater to the level of a systemic inflammation marker prior to treatment with the present composition, or at least a reduction in the rate of increase of a marker of systemic inflammation by at least about 1% or more, and preferably a reduction of the rate of increase of a marker of systemic inflammation level by about 5% or more, e.g. by 10%, 30%, 50%, 70%, 90% or greater to the rate of increase of the marker prior to treatment with the present composition.

As used herein, the term "blood cholesterol level" refers to the amount of cholesterol which is present within the circulatory system of an individual and includes low-density lipoprotein (LDL) cholesterol and high-density lipoprotein (HDL) cholesterol. Blood cholesterol level is also commonly referred to as "total blood cholesterol" to indicate the inclusion of both LDL and HDL. Improved blood cholesterol levels is a reduction in the amount of blood cholesterol in an individual by at least about 0.5%, and preferably a reduction of about 1% or more, e.g. by 5%, 10%, 30%, 50%, 70% or greater of the blood cholesterol levels in the individual prior to treatment with the present composition, or a reduction in the rate of rising blood cholesterol level by at least about 1% or more, and preferably a reduction of about 5% or more, e.g. by 10%, 30%, 50%, 70%, 90% or greater to the rate of blood cholesterol increase prior to treatment. As used herein, the term "blood" is intended to include the serum fraction of blood and/or the plasma fraction of blood.

As used herein, the term "blood triglyceride level" refers to the amount of triglycerides which are present within the circulatory system of an individual. Triglycerides are also commonly referred to as triacylglycerols, TG or TAG. Improved blood triglyceride levels is a reduction in the level of blood triglycerides in an individual by at least about 0.5%, and preferably a reduction of about 1% or more, e.g. by 5%, 10%, 30%, 50%, 70% or greater to the level of blood triglycerides prior to treatment with the present composition, or a reduction in the rate of increase of blood triglycerides in the individual by at least about 1% or more, and preferably a reduction in the rate of increase of blood triglyceride level by about 5% or more, e.g. by 10%, 30%, 50%, 70%, 90% or greater compared to the rate of increase of blood triglycerides prior to treatment. Reducing blood cholesterol levels and blood triglyceride levels is generally recognized as a way to reduce the risk of heart disease in an individual.

As used herein, the term "glucose tolerance" refers to the ability and time required for the body to respond to the administration of glucose by clearing excess glucose from the circulation. A common test for measuring glucose tolerance is to perform a glucose tolerance test (GTT) on an individual, which typically involves orally administering 75 g of a glucose solution to a fasted individual and measuring blood glucose levels at intervals between 0 and 2 hours after administration. An individual who is "glucose intolerant", as defined by the World Health Organization, has a 2-hour blood glucose level of between 140 to 199 mg per dL (7.8 to 11.0 mmol/l). An individual who has a 2-hour blood glucose level above 199 mg per dL is also glucose intolerant, but is additionally considered to have type II diabetes. Several different parameters of the GTT may be considered to evaluate the glucose tolerance of an individual, such as the 2-hour blood glucose level, fasting blood glucose level, GTT area under the curve, the max/peak blood glucose concentration obtained by an individual and mean blood glucose level. Improved glucose tolerance is an increase in the amount of glucose tolerance in an individual by at least about 0.5%, and preferably an increase of about 1% or more, e.g. by 5%, 10%, 30%, 50%, 70% or greater of the glucose tolerance of an individual prior to treatment with the present composition, or a reduction in the rate that an individual develops glucose intolerance by at least about 1% or more, and preferably a reduction of glucose tolerance loss by about 5% or more, e.g. by 10%, 30%, 50%, 70%, 90% or greater than the rate of glucose tolerance loss of the individual prior to treatment. Lean mass, blood cholesterol level, blood triglyceride level and glucose tolerance are commonly measured in the fasted state in order to minimize the amount of nutrients which are newly entering circulation from the digestion of food and minimize the amount of nutrients which have yet to be been cleared from the blood following ingestion of food.

In another embodiment, a method is provided for increasing lean mass, muscle strength, cognition and glucose tolerance, and reducing systemic inflammation levels, blood cholesterol levels and blood triglyceride levels in an individual, comprising administering to the individual the present multi-nutrient composition.

In another embodiment, a method is provided for increasing cognition and improving at least one of the following in an individual: lean mass, muscle strength, systemic inflammation levels, blood cholesterol levels, blood triglyceride levels and glucose tolerance, comprising administering to the individual the present multi-nutrient composition.

In a further embodiment, a method is provided of improving muscle strength, cognition and systemic inflammation levels, in an individual, comprising administering to the individual the present multi-nutrient composition, wherein the individual performs exercise. The term "exercise" is meant to encompass endurance exercise, high-intensity interval training, resistance exercise, and the like, e.g. exercise that achieves a level of working of at least about 3-6 metabolic equivalents (METS), and combinations thereof (e.g. any combination of endurance exercise, high-intensity interval exercise, or >50% of the one repetition maximum (resistance exercise)). METS is the energy expenditure of a physical activity or exercise defined as the ratio of the metabolic rate of an exercising individual (and therefore the rate of energy consumption) during a specific physical activity to a reference basal metabolic rate. In a preferred embodiment, the exercise is performed on a regular basis. Regularly performing exercise refers to the performance of exercise for a duration of at least a month and preferably chronically such as for 2, 4 or 6 or more months, at a frequency of at least 2 days/week, and preferably at least 3 or more days a week, for a period of at least 30 consecutive minutes per day, preferably 45 minutes or greater, such as 60 minutes or greater, or 75-90 minutes or more. Exercise may include endurance activities such as brisk walking, jogging, running, dancing, swimming, bicycling, sports, interval training, resistance exercise, and the like. Interval training refers to repetitive bouts of exercise that may be at high or lower intensity provided it meets minimal METS requirements. High intensity interval training would include activities such as sprints (e.g. 10 second to 4 minute sprints) followed by a recovery time (e.g. of 10 seconds to 4 minutes). The term "resistance exercise" refers to weight training or other resistance exercise (plyometrics, hydraulic machines, etc.) with a resistance of at least 50% of the one repetition maximum, performed in sets of repetitions (for example, 8-15 repetitions), followed by a recovery between sets, for a period of time sufficient to achieve minimal METS requirements. One repetition maximum is the maximal voluntary contraction strength for a single movement where a second movement is impossible.

The multi-nutrient composition may be administered at any time relative to the performance of exercise, i.e. before, during or following the exercise, or any combination thereof. In one embodiment, the multi-nutrient composition is administered to an individual immediately following exercise.

Unless otherwise indicated, the definitions and embodiments described in this and other sections are intended to be applicable to all embodiments and aspects of the present application herein described for which they are suitable as would be understood by a person skilled in the art.

EXAMPLES

The following non-limiting examples are illustrative of the present application. While the present application has been described with reference to examples, it is to be understood that the scope of the claims should not be limited by the embodiments set forth in the examples, but should be given the broadest interpretation consistent with the description as a whole.

All references referred to herein are incorporated by reference in their entirety to the same extent as if each reference was specifically and individually indicated to be incorporated by reference in its entirety. Where a term in the present application is found to be defined differently in a document incorporated herein by reference, the definition provided herein is to serve as the definition for the term.

Example 1—Multi-Nutrient Composition Improves Lean Mass, Muscle Strength, Cognition, Systemic Inflammation Levels, Blood Cholesterol Levels, Blood Triglyceride Levels and Glucose Tolerance in a Randomized, Double-Blind, Placebo-Controlled, Trial To determine if the daily consumption of a multi-nutrient composition containing protein, creatine, calcium, vitamin D and n-3 fatty acids could: 1) stimulate gains in strength, physical function, lean mass, and metabolic health in a group of healthy individuals following 6 weeks of supplementation alone; and/or 2) enhance exercise-mediated gains in strength, physical function, lean mass, and metabolic health following a 12-week combined RET+HIIT program, a randomized, double-blind, placebo-controlled, parallel group trial was conducted.

Methods

Screening and Recruitment

Forty-nine healthy older men from Hamilton, Ontario and its surrounding area took part in this study. Interested individuals who responded to newspaper advertisements were screened first by telephone to inquire if they were non-smokers ≥65 years old, had a body mass index (BMI) in the normal-overweight range (between 18.5 and 30.0 kg/m$^2$), and had not participated in any structured resistance or aerobic exercise training program in the past 6 months. Exclusion criteria included: regular consumption of whey protein, creatine, calcium, vitamin D or n-3 fatty acid supplements in the past 5 years; significant weight loss or gain in the past 6 months; use of non-steroidal anti-inflammatory drugs, simvastatin, or prescription-grade blood thinners; injuries preventing safe participation in an exercise program; diabetes mellitus; cancer; infectious disease; and cardiac or gastrointestinal problems.

Individuals who passed the preliminary telephone screening were invited to McMaster University for a secondary medical screening. To confirm eligibility, subjects were required to be non-diabetic based on a 2-hour, 75 g oral glucose tolerance test (OGTT; having a fasting blood glucose <7.0 mM and 2-hour blood glucose <11.1 mM) and demonstrate normal cardiac function during a maximal exercise stress test on a cycle ergometer. This trial was approved by the Hamilton Integrated Research Ethics Board and complied with the guidelines set out in the Declaration of Helsinki. All participants were informed of the nature and possible risks of the experimental procedures before their written informed consent was obtained. Further details concerning the flow of participants through this study can be found in FIG. 1.

Experimental Design

Figure 2:
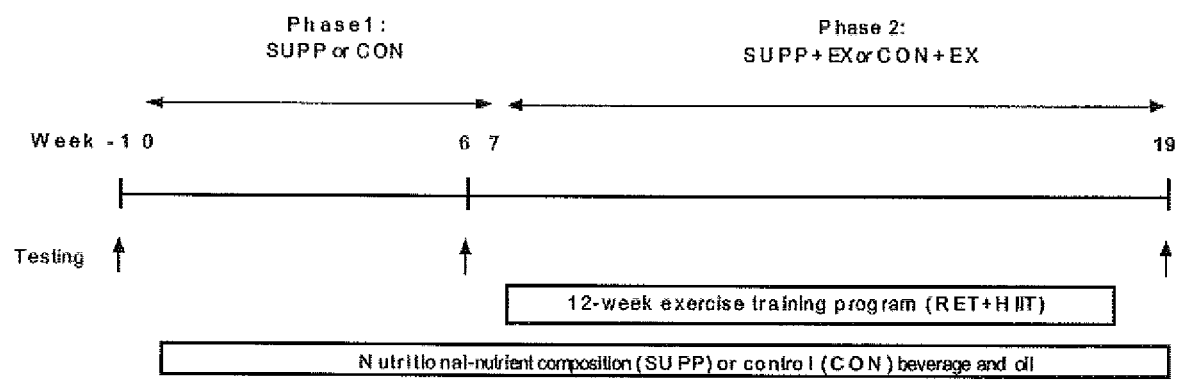
FIG. 2 illustrates a schematic of the study design where participants consumed either a multi-nutrient composition (SUPP) or control (CON) beverage for 19 weeks total (from weeks 0-19, inclusive), and completed a 12-week exercise training program (RET twice per week and HIIT once per week) during weeks 7-18. Testing occurred at weeks −1 (baseline), 6, and 19. Phase 1 (SUPP or CON) took place between weeks 0-6 (sedentary, post-supplement), and Phase 2 (SUPP+EX or CON+EX) took place between weeks 7-19 (post exercise trained, post-supplement).

Eligible subjects were randomly assigned to receive either a multi-nutrient composition (SUPP) or a control (CON) beverage for 19 weeks twice a day, with either an n-3 fatty acid oil or control oil administered once daily (see FIG. 2). After 6 weeks of consuming their study beverages at home (Phase 1), subjects completed a 12-week supervised exercise training program at McMaster University while continuing to consume their assigned beverages (Phase 2). Testing occurred at weeks -1 (baseline), 6, and 19. The following assessments were conducted over the course of each testing week: muscle strength, aerobic fitness, physical function, body composition, blood metabolite levels, markers of systemic inflammation levels, a 75 g OGTT, dietary intake, habitual physical activity and various aspects of cognition (including memory, executive function, and processing speed).

Nutritional Supplements

The multi-nutrient composition used in the study included whey protein, creatine, calcium, vitamin D and n-3 fatty acids. All ingredients except for the n-3 fatty acids (and control oil) were packaged in powder form in individual sachets to be mixed with water prior to consumption. Subjects were instructed to prepare the study beverages at home by mixing the contents of 1 sachet with 250-600 mL water, and to consume a total of 2 study beverages per day: the first 1 h after breakfast, and the second 1 h before bed. Due to difficulties emulsifying oil and water, the n-3 fatty acids and control oil (sunflower oil) were packaged separately in bottles. Subjects were also instructed to measure out and consume 10 mL of oil once per day (which delivered 3.0 g n-3 fatty acids: 1.4 g eicosapentaenoic acid [EPA] and 0.890 g docosahexaenoic acid [DHA]) with their morning study beverage. The control powder and oil were matched in volume and flavour to the active forms. Subjects in the SUPP group received 60 g of whey protein, 5 g of creatine, 800 mg of calcium, 1000 IU vitamin D, 1400 mg EPA and 890 mg DHA daily. Subjects in the CON group received control versions of both the beverages and oil which contained no appreciable amount of whey protein, creatine, calcium, vitamin D, EPA and DHA. Further information pertaining to the composition of and nutrition information for the multi-nutrient composition and control beverages and oils is shown in Table 1. All study beverages and oils were prepared and labeled by Infinit Nutrition (Windsor, ON). Both subjects and researchers were blind to individual group assignments. Participants were instructed not to alter their dietary or physical activity habits for the duration of the study.

TABLE 1

Nutritional composition of the study beverages and oils

| | Per day (2 drinks and oil administration) | |
|---|---|---|
| | SUPP | CON |
| Whey protein (g) | 60 | 0 |
| Creatine (g) | 5 | 0 |
| Calcium (mg) | 800 | 0 |
| Vitamin D (IU) | 1000 | 0 |
| n-3 PUFA (g) | 3 | 0 |
| Carbohydrate (g) | 2 | 44 |
| Energy (kcal) | 210 | 112 |

SUPP, multi-nutrient composition;
CON, control

Prior to beginning the study, participants were provided with a journal to record their daily beverage and oil intake. Participants were also provided with the full amount of sachets and oil required to complete the trial. This amount included a known number of extra sachets and oil bottles, and subjects were instructed to keep and return all unused sachets and oil bottles when their participation in the study ended. Compliance with the study beverages (SUPP group: 87±2%; CON group: 92±2%) and oils (SUPP group: 92±2%; CON group: 95±2%) was high and verified via self-report in the beverage/oil journals, as well as based on the volume of unused beverage sachets/oil returned upon completion or withdrawal.

Exercise Training

From weeks 7 to 18 (phase 2), subjects engaged in a 12-week progressive exercise training program at the Physical Activity Centre of Excellence (PACE) at McMaster University. Subjects completed three supervised exercise sessions per week: RET twice per week (Mondays and Fridays) and HITT once per week (Wednesdays).

After a 5 min warm-up on a cycle ergometer, subjects performed 3 sets of 4 separate exercises in the following order: leg press, chest press or lat pull-down, horizontal row or shoulder press, and leg extension. Chest press and horizontal row were only performed on Mondays, and lat pull-down and shoulder press were only performed on Fridays (leg press and leg extension were performed at every RET session). RET sessions were concluded with a 5 min cool-down on a cycle ergometer. During the first 3 weeks of exercise training, workload was gradually increased from 65% 1RM (10-12 repetitions) to 80% 1RM (6-8 repetitions), and this intensity was maintained for the remainder of the study. Throughout the entire training program, set three of each exercise was always completed until volitional fatigue, which was defined as the inability to complete an additional repetition with proper form. Training intensity was adjusted based on 1RM strength tests conducted at weeks 11 and 15. Additionally, to ensure an adequate training stimulus, workload was increased outside of these weeks when subjects could complete ≥12 repetitions during set three.

HIIT was performed on a cycle ergometer (ISO1000 Upright Bike; SCIFIT, Tulsa, Okla.) in conjunction with a chest-mounted heart rate (HR) monitor (117 Heart Rate Sensor; Polar Electra Canada, Lachine, QC). Following a 3 min warm-up at 25 W, subjects completed 10×60 s intervals at a workload predetermined to elicit about 90% maximal HR (HRmax), while maintaining a cadence of ≥90 rpm. Workload was adjusted by 3-5 W as needed to maintain an average HR of about 90% HRmax over the 10 intervals. Intervals were interspersed with 60 s of rest where subjects cycled at a self-selected pace against 25 W. HIIT sessions were concluded with a 5 min cool-down at 25 W.

Subjects in the SUPP and CON groups attended 95±1% and 94±1% of training sessions, respectively. All subjects attended at least 80% of all RET and HIIT sessions.

Strength Assessment

Muscle strength was assessed using 1RM strength tests for the following exercises: leg press, chest press, lat pull-down, horizontal row, shoulder press, and leg extension (HUR; Northbrook, Ill.). At baseline, proper lifting technique was demonstrated to and practiced by participants during a familiarization session, and 1RMs were estimated using the multiple-repetitions testing procedure. Approximately four days later, 1RMs were evaluated as previously described (Mayhew et al. 1995. J Sports Med Phys Fitness, 35(2):108-13). Familiarization sessions were not repeated for subsequent 1RM strength tests (i.e. at weeks 6, 11, 15, and 19); rather, a previous testing or training session was used to estimate the loads to be attempted during 1RM evaluations. Strength is reported as individual 1RMs for each of the six exercises, as well as the sum of upper body 1RMs (horizontal row, chest press, lat pull-down, and shoulder press), the sum of lower body 1RMs (leg extension and leg press), and the sum of all 1RMs.

Cognitive Function

Several different tests were conducted to evaluate cognition including the Montreal Cognitive Assessment (MoCA), the Rey Auditory Verbal Learning Test (RAVLT), the Go-No-Go Task and the Simple Reaction Time Task.

The MoCA was performed as described by Nasreddine et al. (2005. J Am Geriatr Soc., 53(4):695-9.

In the RAVLT, participants were instructed to recall as many words as possible, in any order, from a 15 word list (List A) upon listening to a research assistant read the words aloud. This was repeated 5 consecutive times, and each trial was scored based on the number of correctly recalled words. Next subjects listened to a new 15 word distractor list (List 13) and were asked to recall as many words as possible. Subsequently, participants were asked to recall as many words as possible from List A without hearing them again. Delayed recall of List A was tested following a 30 min time interval. The participants were then presented with a recognition list of 30 words, including the 15 target words from List A, and asked to circle the target words.

In the Go-No-Go Task, which is also known as a working memory inhibitory control task, participants were presented with 120 letters appearing one at a time in the center of a computer screen. They were instructed to press the spacebar ("Go") when they saw any letter except for J, D, V, or M ("No-Go"). These target letters comprised one third of the total number of trials. A jittered presentation of a blank screen preceded the presentation of each letter for 500 ms-1 s. The duration of each trial was 500 ms.

In the Simple Reaction Time Task (Clark et al. 2015. J Am Geriatr Soc., 64(1), 177-9.) participants were presented with 60 letters appearing one at a time in the centre of a computer screen. They were instructed to press the spacebar as quickly as possible anytime a letter appeared on the computer screen. As with the Go-No-Go Task, a jittered presentation of a blank screen preceded the presentation of each letter for 500 ms-1 s, and the duration of each trial was 500 s.

Systemic Inflammation

Fasting plasma TNF-$\alpha$ and IL-6 concentrations were measured using a Bio-Plex system (Bio-Rad Laboratories; Hercules, Calif.), and plasma CRP concentrations were measured using an Express Plus Autoanalyzer (Chiron Diagnostics Co; Walpole, Mass.) and a commercially available high-sensitivity CRP latex kit (Pulse Scientific; Burlington, ON).

Erythrocyte membrane phospholipid composition was measured as described previously (Dirks et al. 2016. Diabetes., 65(10):2862-75). Briefly, total lipids—were extracted from blood samples, and thin layer chromatography was used to separate individual classes of phospholipids. Once isolated, phospholipids were methylated with 1 M methanolic sodium methoxide at room temperature for 10 min, and the fatty acid composition of each class of phospholipids was analyzed by gas chromatography (Hewlett-Packard 5890 Series II System, equipped with a double flame ionization detector, and Agilent CP-Sil 88 capillary column, 100 m, internal diameter of 0.25 mm). Fatty acids were identified by comparing retention times to those of a known standard, and absolute amounts of individual fatty acids were calculated with the aid of an internal standard (pentadecanoic acid), which was added to samples before the methylation process. Total amounts of each phospholipid were determined from the sum of fatty acids in each fraction. EPA+DHA content was determined by summing the total amount of the EPA and DHA in all phospholipid fractions.

The ratio of arachidonic acid to eicosapentaenoic acid (ARA:EPA ratio), an indicator of systemic inflammation, was determined by dividing the total ARA content by the total EPA content. The omega-3 index was calculated as follows:

Omega-3=index=(*EPA+DHA* content)/total *FA*\*100

Aerobic Fitness

Subjects performed an incremental peak oxygen uptake ($VO_2$ peak) test on an electronically braked cycle ergometer (Lode Excalibur Sport V 2.0; Groningen, The Netherlands) while wearing a chest-mounted heart rate monitor. A metabolic cart and online gas collection system (MOXUS Modular Oxygen Uptake System; AEI Technologies, Pittsburgh, Pa.) were used to quantify respiratory gases. Following a 1 min warm-up at 30 W, the load was increased by 1 W every 4 s. Participants were instructed to maintain a cadence of 60-90 rpm, and tests were terminated if the cadence dropped below 55 rpm for >10 s, or if volitional fatigue was attained. $VO_2$ peak was defined as the highest average oxygen uptake over a 30 s period.

Physical Function

Subjects completed 4 assessments designed to gauge the ability to perform activities of daily living. The 30 s chair stand required subjects to rise from a chair without the use of their arms as many times as possible in 30 s. For the timed up-and-go (TUG), subjects were instructed to rise from the same chair, walk to and from a clearly marked point a distance of 3 m away, and sit back down in the shortest amount of time possible. Maximal left and right hand grip strength was recorded using a digital dynamometer (Zona Plus, Zona Health Inc; Boise, Id.) while subjects stood with their feet hip distance apart and their arm bent to 90°. For the TUG and grip strength, the average of 3 trials was recorded, with 2-3 min rest allowed between trials. Subjects were given a practice trial before both the 30 s chair stand and the TUG. Lastly, the 6 min walk test was performed on a 200 m indoor track. Subjects were instructed to attempt to cover as much distance as possible within 6 min while walking in a safe manner.

Body Composition

Whole body and regional lean mass, fat mass and bone mineral content were measured using dual energy X-ray absorptiometry (DXA; GE-LUNAR iDXA; Aymes Medical, Newmarket, ON) following a 10-12 h overnight fast. Regional body compartment analysis was performed in batch by a single investigator who was blinded to group assignment. Waist and hip circumferences were measured at the top of the iliac crests and at the widest portion of the hips, respectively, using a tape measure while participants stood with their arms relaxed and feet together.

Oral Glucose Tolerance Test

After a 10-12 h overnight fast, a 20 G catheter was inserted into an antecubital vein and a fasting blood sample (0 min) was obtained. Subjects then consumed a 75 g dextrose solution (Trutol™; NERL Diagnostics LLC, East Providence, R.I.) within 5 min. Serial blood samples were obtained at 30, 60, 90 and 120 min post-ingestion of the dextrose beverage for the measurement of plasma glucose and insulin concentrations.

Three-Day Food Record

Weighted three-day food records (2 weekdays and 1 weekend day) were analyzed using ESHA (Food Processor Nutrition Analysis Software; Salem, Oreg.). Subjects were instructed by research staff on how to record the types and quantities of food, beverages, study beverages/oil (only for food records of weeks 6 and 19), and other nutrition supplements or vitamins that they consumed during this period. Baseline 3-day food records were completed prior to commencing the study protocol, and therefore are reflective of participants' pre-study habitual dietary intake (i.e. do not include study beverages and oils). The food records completed at weeks 6 and 19 reflect habitual dietary intake plus study beverages and oils consumed on those days. Finally, subjects were instructed to refrain from completing their dietary records on days where they visited McMaster University for testing.

Habitual Physical Activity

A subset of participants (n=10 in the SUPP group and n=12 in the CON group) wore arm-mounted accelerometers (BodyMedia SenseWear Armband, Cardinal Health Canada; Vaughan, ON) for 72 h to estimate daily total energy expenditure (TEE), and other indicators of habitual physical activity such as active energy expenditure (AEE) and average metabolic equivalents (METs). As with the 3-day food records, subjects were instructed to avoid wearing the armbands during testing days.

Biochemical Analysis

All blood analyses were performed by the Core Laboratory at the McMaster University Medical Centre. Plasma glucose concentrations were measured using the glucose oxidase method (YSI 2300; Yellow Springs, Ohio). Plasma insulin concentrations were measured using the dual-site chemiluminescent method (Siemens Immulite 2000; Malvern, Pa.). Cholesterol (total, HDL, and LDL) and triglycerides (TAG) were analyzed using the Architect Clinical Chemistry Analyzer (Abbott Laboratories).

Statistical Analysis

Statistical analysis was completed using SPSS (version 23.0). An intention-to-treat analysis was conducted using a linear mixed model with an unstructured covariance matrix including group (SUPP or CON) and time (weeks −1, 6, and 19) as factors, and respective baseline values as covariates. Significant differences were identified using a Bonferroni post hoc test. Based on recommendations for human clinical trials with missing data (18), all participants (completers as well as participants who withdrew prior to week 6 or week 19 testing) were included in the final analysis, and missing values were not replaced. Differences between the SUPP and CON groups at baseline were compared using an unpaired t-test. Data are presented as mean±SEM. For all assessments of cognitive function, age was included as a covariate. In the case of significant group-by-time interactions for cognitive function assessments, significant between (SUPP or CON) and within (weeks −1, 6, or 19) group differences were identified with Tukey's post hoc test. Statistical significance was accepted as $P<0.05$.

Results

Forty-nine older men were randomized: 38 completed the study and 11 dropped out (n=7 and n=4 dropouts in the SUPP and CON groups, respectively). Of the participants who dropped out, 4 withdrew prior to week 6 testing (during Phase 1), and 7 withdrew partway through the exercise training program and prior to week 19 testing (during Phase 2). Reasons for withdrawal from the study are provided in FIG. 1. Baseline characteristics did not differ between groups, and are presented in Table 2.

TABLE 2

Baseline characteristics of participants

| | SUPP (n = 25) | CON (n = 24) |
|---|---|---|
| Age (years) | 71 ± 1 | 74 ± 1 |
| Systolic BP (mmHg) | 138 ± 4 | 138 ± 3 |
| Diastolic BP (mmHg) | 78 ± 2 | 78 ± 2 |

TABLE 2-continued

Baseline characteristics of participants

|  | SUPP (n = 25) | CON (n = 24) |
|---|---|---|
| Body composition | | |
| Body mass (kg) | 85.3 ± 2.4 | 84.5 ± 2.5 |
| Height (m) | 1.72 ± 0.01 | 1.73 ± 0.01 |
| BMI (kg/m$^2$) | 28.9 ± 0.8 | 28.1 ± 0.7 |
| Lean mass (kg) | 54.0 ± 1.1 | 54.5 ± 1.4 |
| Fat mass (kg) | 28.2 ± 1.7 | 26.8 ± 1.4 |
| % body fat | 33.6 ± 1.3 | 32.6 ± 1.0 |
| Waist:hip ratio | 0.99 ± 0.01 | 0.99 ± 0.01 |
| Fitness | | |
| Leg extension 1RM (kg) | 27 ± 1 | 27 ± 2 |
| Leg press 1RM (kg) | 77 ± 3 | 69 ± 4 |
| VO$_{2peak}$ (mL/kg/min) | 23.8 ± 0.8 | 24.4 ± 0.9 |
| Peak power (watts) | 154 ± 5 | 158 ± 7 |
| Blood analytes | | |
| Fasting glucose (mM) | 5.6 ± 0.1 | 5.8 ± 0.1 |
| 2 hr glucose (mM) | 6.8 ± 0.4 | 7.2 ± 0.4 |
| HOMA-IR | 2.1 ± 0.1 | 2.2 ± 0.1 |
| Cholesterol (mM) | | |
| Total | 4.69 ± 0.22 | 4.83 ± 0.19 |
| LDL | 2.74 ± 0.21 | 2.87 ± 0.18 |
| HDL | 1.27 ± 0.06 | 1.29 ± 0.06 |
| TAG (mM) | 1.49 ± 0.19 | 1.50 ± 0.21 |

Data are mean ± SEM.
SUPP, multi-nutrient composition group;
CON, control group;
BP, blood pressure;
1RM, 1 repetition maximum;
VO$_2$peak, peak oxygen consumption;
TAG, triacylglycerol 1RM Muscle Strength At baseline, no difference in any measure of 1RM muscle strength was observed between the SUPP and CON groups. A significant group x time interaction (indicating that the SUPP and CON groups changed differently over time) was observed for the sum of all 1RMs (P<0.05), upper body 1RMs (P<0.05), and horizontal row 1RM (P<0.01) muscle strength, so groups were analyzed separately for these measures.

Figure 3:
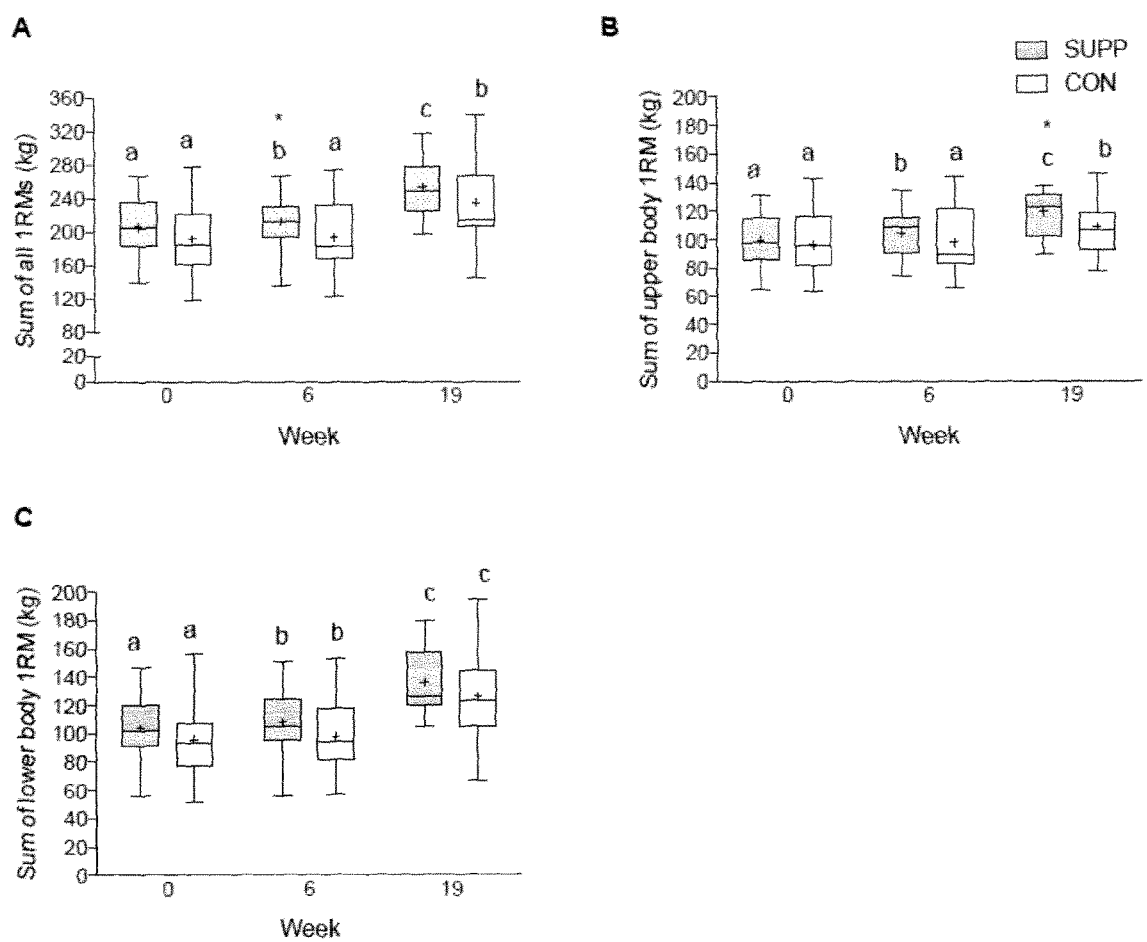
FIG. 3 graphically illustrates the dynamic muscular strength expressed as the (A) sum of all, (B) upper body and (C) lower body 1RMs. Boxes (SUPP: grey; CON: white) represent interquartile ranges, with the horizontal lines indicating the median. Whiskers represent the maximal and minimal values, and crosses indicate the mean. Dissimilar letters denote changes over time within a given treatment group (SUPP or CON). * indicates a significant difference from the CON group at that timepoint. Values are mean±SEM. n=25 for SUPP and n=24 for CON groups.

In the SUPP group, the sum of all 1RMs increased by 3% during Phase 1 (from 206±7 kg at baseline to 212±8 kg at week 6, P<0.001; FIG. 3A) and a further 20% during Phase 2 (from 212±8 kg at week 6 to 254±8 kg at week 19, P<0.001). After phase 1, the sum of all 1RMs for the SUPP group was significantly greater than the CON group. The sum of upper body 1RMs increased by 6% during Phase 1 (from 99±4 kg at baseline to 105±4 kg at week 6, P<0.001; FIG. 3B) and a further 13% during Phase 2 (from 105±4 kg at week 6 to 119±4 kg at week 19, P<0.001). At the end of Phase 2, the sum of upper body 1RMs for the SUPP group was significantly greater than the CON group. Horizontal row 1RM increased by 8% during Phase 1 (from 25±1 kg at baseline to 27±1 kg at week 6, P<0.01), and a further 19% during Phase 2 (from 27±1 kg at week 6 to 32±1 kg at week 19, P<0.001). In the CON group, no change in total (FIG. 3A), upper body (FIG. 3B), or horizontal row (Table 3) 1RM muscle strength was observed as a result of Phase 1. However, following Phase 2 the sum of all 1RMs increased by 21% (from 194±10 kg at week 6 to 235±13 kg at week 19, P<0.001), the sum of upper body 1RMs increased by 11% (from 98±5 kg at week 6 to 109±5 kg at week 19, P<0.001), and horizontal row 1RM increased by 7% (from 27±2 kg at week 6 to 29±1 kg at week 19, P<0.001) in the CON group. A main effect of time for lat pulldown (P<0.001), shoulder press (P<0.01), leg extension (P<0.001), leg press (P<0.001), and the sum of lower body 1RMs (P<0.001) was observed whereby no significant changes occurred following Phase 1, but 1RM muscle strength improved significantly for all exercises in both the SUPP and CON groups over the course of Phase 2 (Table 3). No significant change in chest press 1RM over the course of the study was observed. Surprisingly, these results demonstrate that the multi-nutrient composition significantly improved the muscle strength of healthy individuals after only 6 weeks of administration and that the multi-nutrient composition exerted a synergistic effect when combined with exercise to result in further gains above that seen in the nutritional control groups.

TABLE 3

1RM muscle strength measurements for individual exercises

|  | SUPP | | | CON | | |
|---|---|---|---|---|---|---|
|  | Baseline | 6 wk | 19 wk | Baseline | 6 wk | 19 wk |
| Leg extension (kg)$^2$ | 27 ± 1$^a$ | 29 ± 2$^a$ | 39 ± 2$^b$ | 27 ± 2$^a$ | 28 ± 2$^a$ | 36 ± 2$^b$ |
| Leg press (kg)$^2$ | 77 ± 3$^a$ | 80 ± 5$^a$ | 98 ± 5$^b$ | 69 ± 4$^a$ | 70 ± 5$^a$ | 91 ± 7$^b$ |
| Chest press (kg) | 22 ± 1 | 22 ± 1 | 27 ± 1 | 19 ± 1 | 21 ± 1 | 24 ± 2 |
| Horizontal row (kg)$^1$ | 25 ± 1$^a$ | 27 ± 1$^b$ | 32 ± 1$^c$ | 26 ± 1$^a$ | 27 ± 2$^a$ | 29 ± 1$^b$ |
| Lat pull-down (kg)$^2$ | 26 ± 1$^a$ | 27 ± 1$^a$ | 31 ± 1$^b$ | 27 ± 2$^a$ | 27 ± 2$^a$ | 30 ± 1$^b$ |
| Shoulder press (kg)$^2$ | 26 ± 1$^a$ | 27 ± 2$^a$ | 29 ± 2$^b$ | 24 ± 2$^a$ | 24 ± 2$^a$ | 26 ± 2$^b$ |

Values are mean ± SEM.
[1]Group x time interaction (P < 0.01).
[2]Main effect for time (P < 0.01).
For each outcome, different letters represent significant differences within each group.
Significance accepted as P < 0.05.
1RM, 1 repetition maximum; SUPP, multi-nutrient composition group; CON, control group Body Composition At baseline, no significant differences in body mass or any measurement of body composition were observed between the SUPP and CON groups (Table 4). Significant group x time interactions were detected for whole body lean mass (P<0.01), appendicular lean mass (P<0.05), leg lean mass (P<0.05), and trunk lean mass (P<0.01) over the course of the study, so each group was analyzed separately for these measures.

Cognitive Function

To evaluate cognitive function, four different tests were performed to measure some of the different aspects of cognition. The RAVLT test was performed to evaluate memory, the Go-No-Go Task to evaluate executive functions, the Simple Reaction Time Task to evaluate processing speed and the MoCA was performed as a more general measure of cognitive ability, which evaluates mental skills such as attention and concentration, executive functions,

TABLE 4

DXA regional body compartment analysis and anthropometry

| | SUPP | | | CON | | |
|---|---|---|---|---|---|---|
| | Baseline | 6 wk | 19 wk | Baseline | 6 wk | 19 wk |
| Body mass (kg)$^2$ | 85.3 ± 2.4$^a$ | 85.9 ± 2.6$^b$ | 83.1 ± 2.6$^{a,\,b}$ | 84.5 ± 2.5$^a$ | 85.3 ± 2.7$^b$ | 85.9 ± 2.8$^{a,\,b}$ |
| BMI (kg/m$^2$)$^2$ | 28.9 ± 0.8$^a$ | 29.2 ± 0.8$^b$ | 28.9 ± 0.9$^{a,\,b}$ | 28.1 ± 0.7$^a$ | 28.4 ± 0.8$^b$ | 28.5 ± 0.8$^{a,\,b}$ |
| Fat mass (kg)$^2$ | 28.2 ± 1.7$^a$ | 28.0 ± 1.9$^b$ | 25.9 ± 2.0$^a$ | 26.8 ± 1.4$^a$ | 27.5 ± 1.5$^b$ | 27.5 ± 1.6$^a$ |
| % body fat$^2$ | 33.6 ± 1.3$^{a,\,b}$ | 33.2 ± 1.4$^a$ | 31.7 ± 1.6$^b$ | 32.6 ± 1.0$^{a,\,b}$ | 33.0 ± 1.1$^a$ | 32.9 ± 1.1$^b$ |
| Leg fat mass (kg)$^2$ | 6.9 ± 0.4$^a$ | 6.8 ± 0.5$^b$ | 6.3 ± 0.5$^a$ | 6.5 ± 0.3$^a$ | 6.7 ± 0.4$^b$ | 6.7 ± 0.4$^a$ |
| Leg % fat$^1$ | 26.5 ± 1.0$^a$ | 25.9 ± 1.1$^a$ | 24.5 ± 1.3$^b$ | 25.4 ± 0.7$^a$ | 25.8 ± 0.9$^{b,\,c}$ | 25.5 ± 1.0$^{a,\,c}$ |
| Arm lean mass (kg)$^2$ | 6.3 ± 0.2$^a$ | 6.4 ± 0.2$^b$ | 6.4 ± 0.2$^b$ | 6.3 ± 0.2$^a$ | 6.4 ± 0.2$^b$ | 6.5 ± 0.2$^b$ |
| Arm fat mass (kg) | 2.5 ± 0.2 | 2.5 ± 0.2 | 2.3 ± 0.2 | 2.5 ± 0.1 | 2.5 ± 0.1 | 2.5 ± 0.2 |
| Arm % fat$^2$ | 27.6 ± 1.1$^{a,\,c}$ | 27.4 ± 1.3$^{b,\,c}$ | 26.2 ± 1.4$^a$ | 28.0 ± 1.0$^{a,\,c}$ | 27.9 ± 1.1$^{b,\,c}$ | 27.9 ± 1.1$^a$ |
| Appendicular fat mass (kg)$^2$ | 9.4 ± 0.6$^a$ | 9.3 ± 0.6$^b$ | 8.6 ± 0.7$^a$ | 9.0 ± 0.4$^a$ | 9.2 ± 0.5$^b$ | 9.3 ± 0.5$^a$ |
| Trunk lean mass (kg)$^1$ | 25.1 ± 0.5$^a$ | 25.5 ± 0.6$^b$ | 25.2 ± 0.6$^b$ | 25.5 ± 0.6$^a$ | 25.4 ± 0.6$^a$ | 25.5 ± 0.7$^a$ |
| Trunk fat mass (kg)$^2$ | 17.7 ± 1.2$^{a,\,c}$ | 17.6 ± 1.3$^{b,\,c}$ | 16.2 ± 1.4$^a$ | 16.8 ± 1.0$^{a,\,c}$ | 17.2 ± 1.1$^{b,\,c}$ | 17.2 ± 1.2$^a$ |
| Trunk % fat | 40.3 ± 1.6 | 39.8 ± 1.8 | 38.1 ± 2.0 | 39.0 ± 1.4 | 39.5 ± 1.5 | 39.4 ± 1.6 |
| Waist circumference (cm) | 105.0 ± 1.8 | 105.3 ± 2.0 | 104.3 ± 2.0 | 104.1 ± 1.7 | 104.6 ± 1.9 | 103.8 ± 2.2 |
| Hip circumference (cm) | 106.3 ± 1.1 | 106.6 ± 1.3 | 106.8 ± 1.3 | 105.7 ± 1.4 | 105.7 ± 1.7 | 106.6 ± 1.7 |
| Waist:hip ratio$^2$ | 0.99 ± 0.01$^{a,\,c}$ | 0.99 ± 0.01$^{b,\,c}$ | 0.97 ± 0.01$^a$ | 0.99 ± 0.01$^{a,\,c}$ | 0.99 ± 0.01$^{b,\,c}$ | 0.97 ± 0.01$^a$ |

Figure 4:
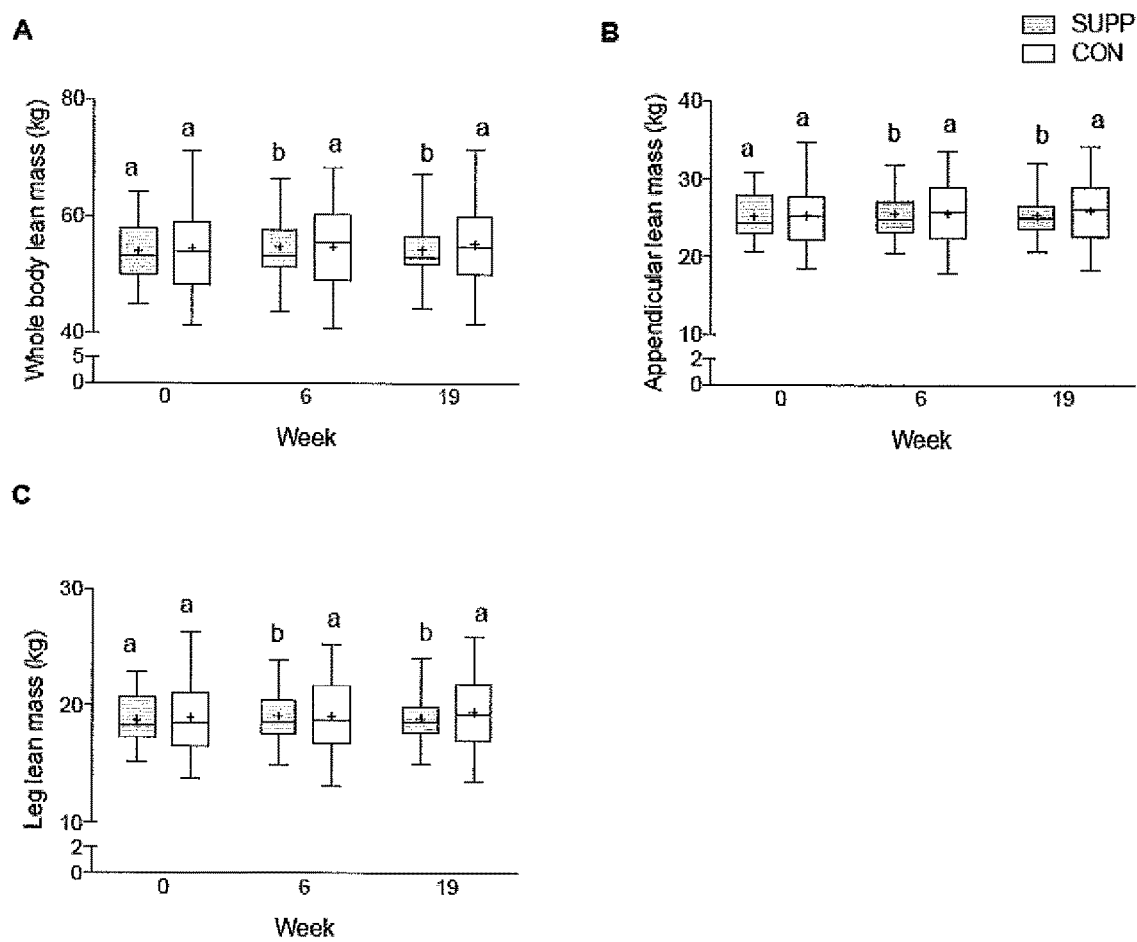
FIG. 4 graphically illustrates (A) whole body, (B) appendicular and (C) leg lean mass. Boxes (SUPP: grey; CON: white) represent interquartile ranges, with the horizontal lines indicating the median. Whiskers represent the maximal and minimal values, and crosses indicate the mean. Dissimilar letters denote changes over time within a given treatment group (SUPP or CON). Values are mean±SEM. n=25 for SUPP and n=24 for CON groups.

Values are mean ± SEM.
$^1$Group x time interaction (P < 0.05).
$^2$Main effect for time (P < 0.05).
For each outcome, different letters represent significant differences within each group.
Significance accepted as P < 0.05.
DXA, dual-energy X-ray absorptiometry; SUPP, multi-nutrient composition group; CON, control group In the SUPP group, whole body lean mass increased by 0.7 kg in response to Phase 1 (from 54.0±1.1 kg at baseline to 54.7±1.2 kg at week 6, P<0.001; FIG. 4A), however no further significant increase was observed during Phase 2. Likewise, appendicular lean mass increased significantly by 0.4 kg (from 25.1±0.6 kg at baseline to 25.5±0.6 kg at week 6, P<0.01; FIG. 4B), leg lean mass increased by 0.3 kg (from 18.8±0.5 kg at baseline to 19.1±0.5 kg at week 6, P<0.01; FIG. 4C), and trunk lean mass increased by 0.4 kg (from 25.1±0.5 kg at baseline to 25.5±0.6 kg at week 6, P<0.01; Table 4) in the SUPP group as a result of Phase 1. However, no further changes in appendicular, leg, or trunk lean mass were observed during Phase 2 in the SUPP group. In the CON group, conversely, no significant change in whole body lean mass (from 54.5±1.4 kg at baseline, to 54.7±1.4 kg at week 6, to 55.2±1.5 kg at week 19, P>0.05; FIG. 4A) or regional measurements of lean mass were detected over the course of the study. Thus, 6 weeks of the multi-nutrient composition was sufficient to significantly improve the lean mass of individuals in comparison to a control group.

No significant differences between the SUPP or CON groups at baseline, week 6 or week 19 were detected for whole body fat mass or appendicular fat mass.

memory, language, visuoconstructional skills, conceptual thinking, calculations and orientation.

Figure 5:
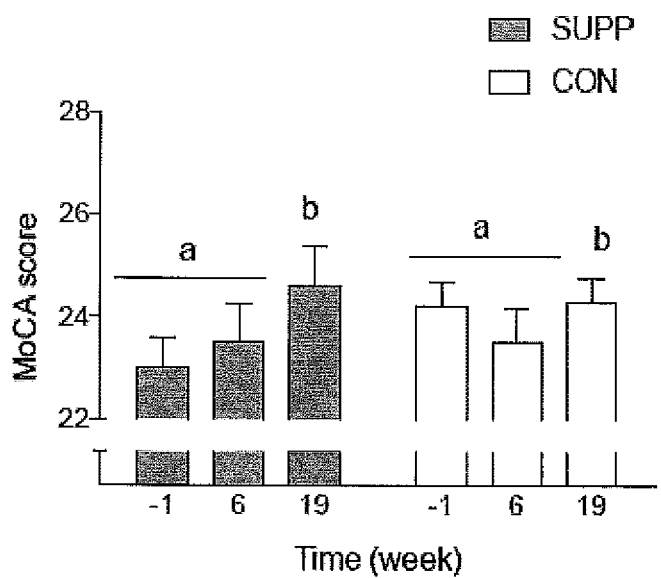
FIG. 5 graphically illustrates a measure of global cognitive ability (assessed using the Montreal Cognitive Assessment (MocA)). Grey bars represent the multi-nutrient composition (SUPP) group; white bars represent the control (CON) group. Dissimilar letters denote changes over time within a given treatment group (SUPP or CON). Values are mean±SEM. n=25 for SUPP and n=24 for CON groups.

No differences were observed for any of the measures of cognition at baseline (FIG. 5). By the end of Phase 2, the MoCA assessment score was significantly improved in SUPP group, whereas no changes were seen in the CON group when compared to baseline.

Figure 6:
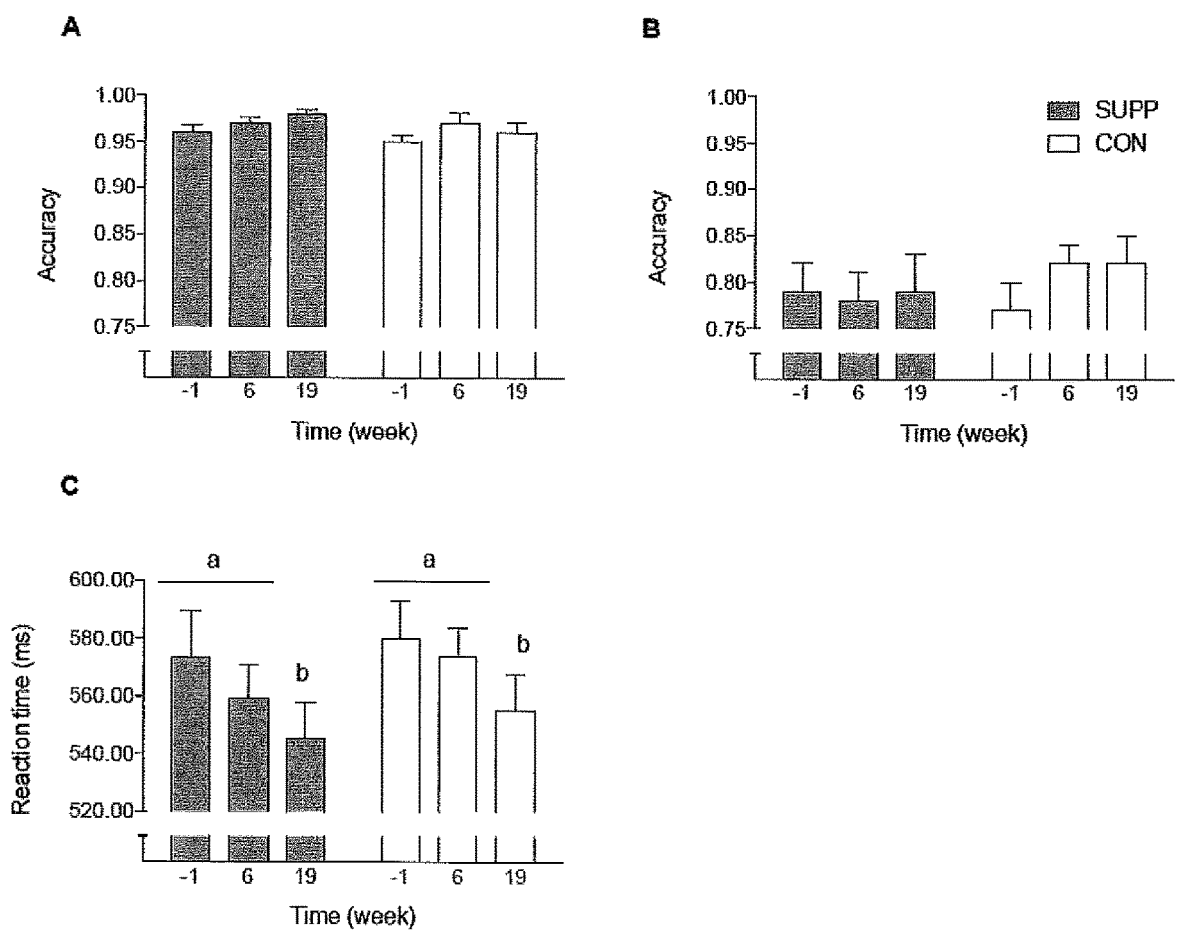
FIG. 6 graphically illustrates working memory inhibition control (assessed using the Go-No-Go Task). Panels indicate: (A) accuracy during the "Go" trials; (B) accuracy during the "NoGo" trials; and (C) mean reaction time during all trials. Accuracy is defined as the proportion of correct responses. Grey bars represent the multi-nutrient composition (SUPP) group; white bars represent the control (CON) group. Dissimilar letters denote changes over time within a given treatment group (SUPP or CON). Values are mean±SEM. n=25 for SUPP and n=24 for CON groups.

For the Go-No-Go Task, there was a strong trend (p=0.057) towards a reduction in reaction time after Phase 1 in the SUPP group, and reaction times were significantly lowered in the SUPP group by the end of phase 2 (FIG. 6A/B) as shown by an increase in number of correct responses which is inversely related to reaction time. In contrast, reaction times were only lower in the CON group after the end of Phase 2.

Figure 7:
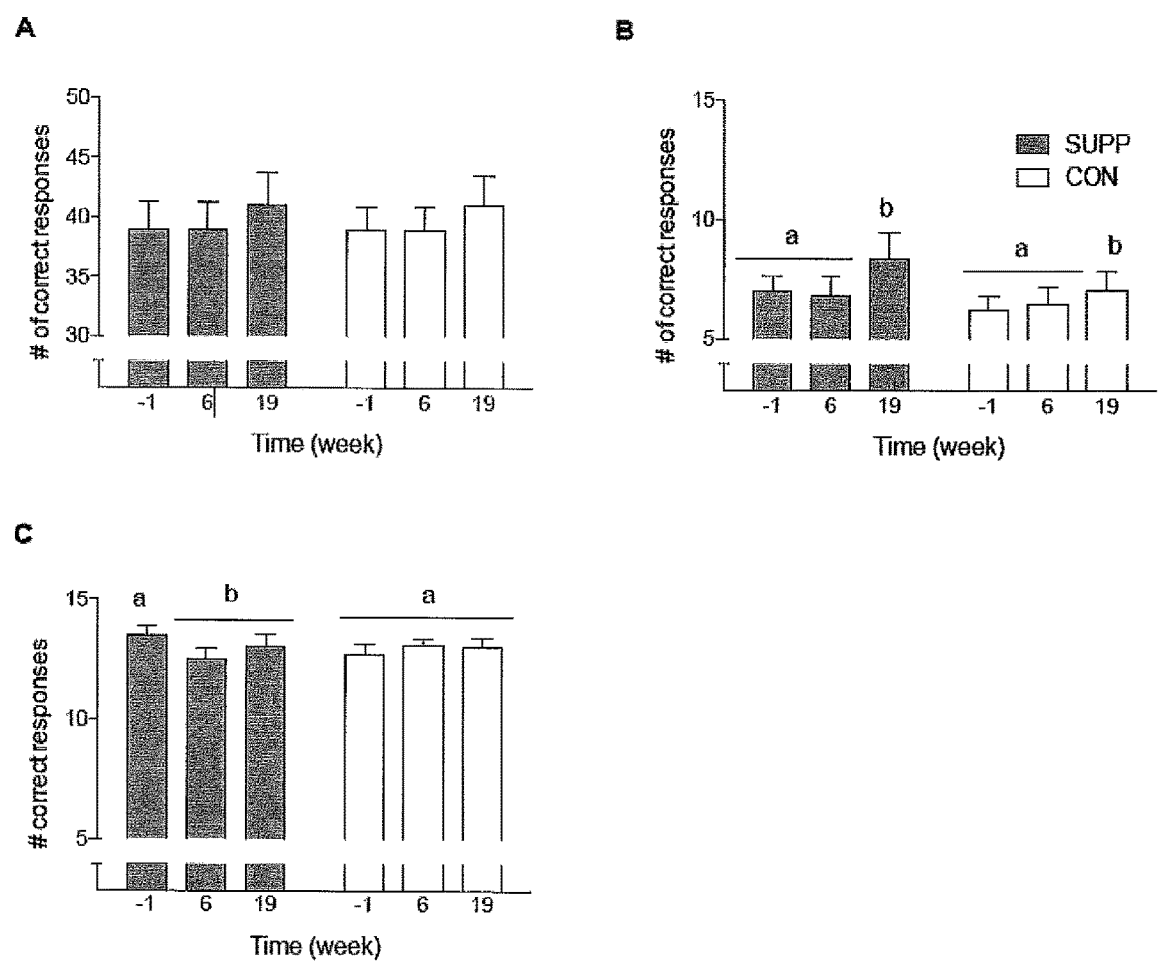
FIG. 7 graphically illustrates verbal memory performance (assessed using the Rey Auditory Verbal Learning Test). Panels indicate the number of words: A) correctly recalled over the course of 5 trials (out of a possible 75 point total), B) correctly recalled following a 30 min delay (out of a possible 15 point total and recognized on a written list) and C) recognized on a written list (out of a possible 15 point total), Grey bars represent the multi-nutrient composition (SUPP) group; white bars represent the control (CON) group. Dissimilar letters denote changes over time within a given treatment group (SUPP or CON). Values are mean±SEM. n=25 for SUPP and n=24 for CON groups.

For the RAVLT testing, the number of words recalled after a delay was significantly higher following phase 2 of the study in the SUPP group, with no changes occurring in the CON group (FIG. 7C).

No differences of reaction time were noted for the Simple Reaction Time Task between either SUPP or CON groups (Table 5).

TABLE 5

Simple Reaction Time performance.

| | SUPP | | | CON | | |
|---|---|---|---|---|---|---|
| | Baseline | 6 wk | 19 wk | Baseline | 6 wk | 19 wk |
| Simple Reaction Time Task | | | | | | |
| Reaction time (ms) | 288.77 ± 11.03 | 299.83 ± 16.20 | 286.74 ± 10.37 | 300.05 ± 9.89 | 302.70 ± 9.34 | 290.14 ± 8.18 |
| Accuracy[1] | 0.99 ± 0.00 | 0.99 ± 0.00 | 0.99 + 0.00 | 0.99 ± 0.00 | 0.99 ± 0.00 | 0.98 ± 0.00 |

Data are mean ± SEM, No significant differences.
[1]Accuracy refers to the proportion of correct responses. SUPP, multi-nutrient composition; CON, control Accuracy values for the MoCA and memory test (RAVLT), and inverse reaction time for the executive functions test (Go-NoGo task), were normalized and averaged together to create a composite score for global cognition. Using one-sample t tests it was evaluated whether the post-minus-pre change in global cognition was significantly different from no change (i.e., zero). A significant improvement in the composite score of cognition was observed for the SUPP group, but not the CON group.

Figure 8:
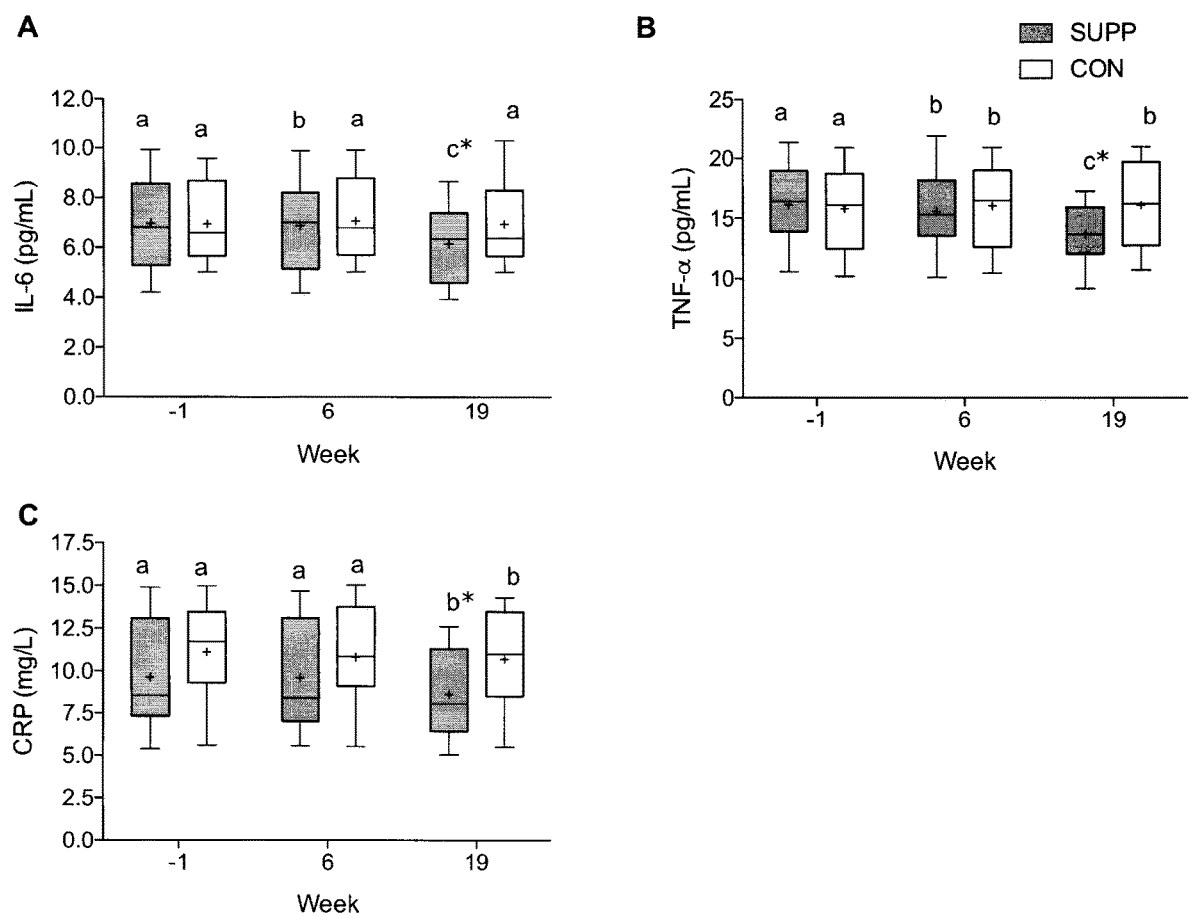
FIG. 8 graphically illustrates plasma (A) IL-6, (B) TNF-alpha and (C) CRP concentrations throughout the study. Boxes (SUPP: grey; CON: white) represent interquartile ranges, with the horizontal lines indicating the median. Whiskers represent the maximal and minimal values, and crosses indicate the mean. Dissimilar letters denote changes over time within a given treatment group (SUPP or CON). * indicates a significant difference from the CON group at that timepoint. Values are mean±SEM. n=25 for SUPP and n=24 for CON groups.

Overall, these findings demonstrate surprisingly that the multi-nutrient composition improved cognition in healthy individuals following 6 weeks of use, and that these effects were improved further by administering the composition in conjunction with exercise, Systemic Inflammation At baseline, there were no differences in inflammatory markers between groups. Significant group-by-time interactions for CRP ($P<0.001$), TNF-α ($P<0.001$), and IL-6 ($P<0.001$) were observed (FIG. 8). In both the SUPP and CON groups, plasma CRP concentrations did not change in Phase 1; although significant reductions were observed in both groups following Phase 2, the magnitude of this change was numerically larger in the SUPP group (SUPP: −10% and CON: −1%; $P<0.05$; FIG. 8. In the SUPP group, mean plasma TNF-α and IL-6 concentrations each decreased ~1-3% during Phase 1 and a further ~11-12% in response to Phase 2. In the CON group, plasma TNF-α and IL-6 concentrations did not improve (decrease) over the course of the study. Plasma CRP, TNF-α, and IL-6 concentrations were all significantly lower in the SUPP group compared to the CON group at week 19.

At baseline, omega-3 index was significantly lower in the SUPP versus CON group (P=0.038; Table 6). Significant group-by-time interactions for EPA+DHA content, the ratio of ARA:EPA, and omega-3 index (all $P<0.001$) were observed. In the SUPP group, EPA+DHA content and omega-3 index increased 60-70% during Phase 1 (both $P<0.001$), and a further 10-20% during Phase 2 (both $P<0.001$), The ratio of ARA:EPA was reduced following Phase 1 ($P<0.001$), and this reduction was maintained throughout Phase 2. At weeks 6 and 19, EPA+DHA content and omega-3 index were significantly higher, and the ratio of ARA:EPA was significantly lower, in the SUPP versus CON group. In the CON group, EPA+DHA content, omega-3 index, and the ratio of ARA:EPA did not change over the course of the study. Total FA content did not change in either group throughout the study. These data demonstrate that systemic inflammation is significantly lower following administration of the multi-nutrient composition, and that systemic effects were improved further when the multi-nutrient composition was administered to individuals performing exercise.

TABLE 6

Indicators of EPA and DHA incorporation into erythrocyte plasma membranes

| | SUPP | | | CON | | |
|---|---|---|---|---|---|---|
| | Baseline | 6 wk | 19 wk | Baseline | 6 wk | 19 wk |
| Total FA (pmol/mg Hb) | 10,550.94 ± 505.5 | 9791.93 ± 547.30 | 9639.91 ± 556.33 | 10,098.13 ± 501.95 | 9259.02 ± 447.54 | 9522.98 ± 386.24 |
| EPA + DHA (pmol/mg Hb)[1] | 495.96 ± 27.72$^a$ | 798.02 ± 78.50$^{b*}$ | 881.83 ± 62.83$^{c*}$ | 560.05 ± 35.60$^a$ | 470.98 ± 32.2$^a$ | 458.15 ± 28.30$^a$ |
| ARA:EPA[1] | 140.36 ± 8.78$^a$ | 68.82 ± 8.98$^{b*}$ | 55.02 ± 13.28$^{b*}$ | 127.54 ± 11.35$^a$ | 146.90 ± 10.54$^a$ | 150.57 ± 8.41$^a$ |
| Omega-3 index (%)[1] | 4.7 ± 0.2$^{a*}$ | 8.0 ± 0.4$^{b*}$ | 9.3 ± 0.6$^{c*}$ | 5.6 ± 0.3$^a$ | 5.1 ± 0.2$^a$ | 4.8 ± 0.2$^a$ |

Data are mean ± SEM.
[1]Group-by-time interaction ($P < 0.001$). Different letters denote significant differences over time within each group.
*Significant difference from CON at that time point. SUPP, multi-nutrient composition; CON, control; FA, fatty acid; Hb, hemoglobin; EPA, eicosapentanoic acid; DHA, docosahexanoic acid; ARA, arachidonic acid.

Physical Function and Aerobic Fitness

At baseline, there were no differences in any measure of physical function (Table 7) or aerobic fitness (Table 8) between the SUPP and CON groups. A main effect of time was observed for the TUG ($P<0.001$), the 6 min walk test ($P<0.001$), $VO_2$ peak ($P<0.001$), and peak power ($P<0.001$). Post-hoc testing revealed that no significant changes occurred as a result of Phase 1, however significant improvements were made following Phase 2. Between weeks 6 and 19, the time taken to complete the TUG decreased by 0.31 s (SUPP: −7% and CON: −3%; $P<0.01$). The distance covered in the 6 min walk test increased by 25 m ($P<0.001$) during Phase 2. In addition, relative $VO_2$ peak increased overall by 1.8 mL/kg/min ($P<0.001$), and peak power increased by 13 W. No significant changes in the 30 s chair stand test, left or right grip strength, resting or maximal HR, or RER were observed over the course of study.

Glucose Tolerance

Figure 9:
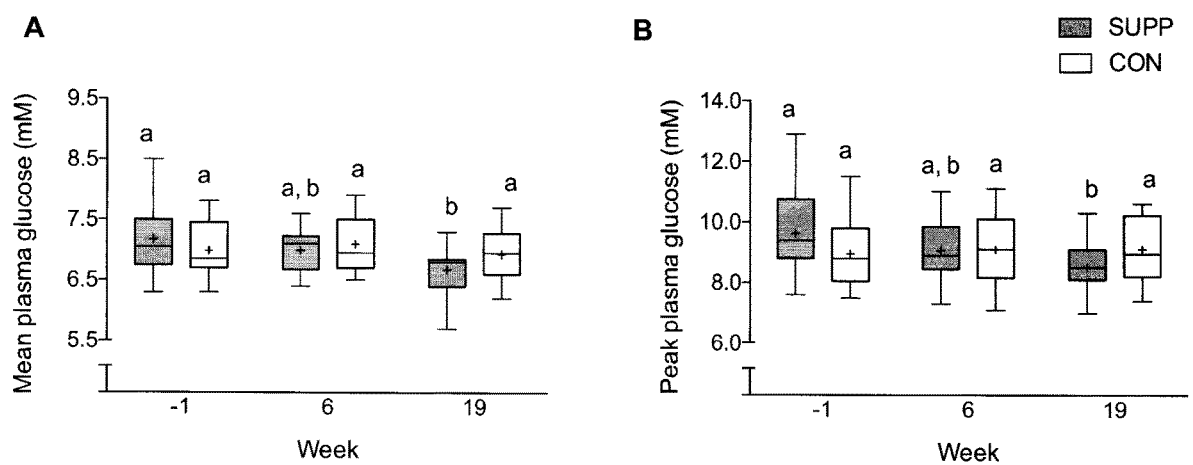
FIG. 9 graphically illustrates (A) mean plasma glucose and (B) peak plasma glucose during GTT. Boxes (SUPP: grey; CON: white) represent interquartile ranges, with the horizontal lines indicating the median. Whiskers represent the maximal and minimal values, and crosses indicate the mean. Dissimilar letters denote changes over time within a given treatment group (SUPP or CON). Values are mean±SEM. n=25 for SUPP and n=24 for CON groups.

At baseline, no significant differences in glucose tolerance or indicators of insulin sensitivity (Table 9) existed between the SUPP and CON groups. A main effect of time was observed for glucose AUC ($P<0.01$), insulin AUC ($P<0.001$), HOMA-IR ($P<0.001$), and the Matsuda index of insulin sensitivity ($P<0.001$). During Phase 2, a reduction in glucose (SUPP: −5% and CON −3%; $P<0.05$) and insulin AUC (SUPP: −11% and CON: −14%; $P<0.001$), and a reduction in HOMA-IR (SUPPP: −20% and CON: −15%; $P<0.001$), as well an increase in the Matsuda Index of insulin sensitivity (SUPP: +20% and CON: +19%; $P<0.001$) was observed. Maximal plasma glucose concentration (FIG. 9A) and mean plasma glucose (FIG. 9B) were lowered in the SUPP group during Phase 2, while no changes occurred in these measures in the CON group. These data show that

TABLE 7

Physical function assessments

| | SUPP | | | CON | | |
|---|---|---|---|---|---|---|
| | Baseline | 6 wk | 19 wk | Baseline | 6 wk | 19 wk |
| 30s chair stand (# stands)[1] | $12 \pm 0^a$ | $13 \pm 1^{a,b}$ | $13 \pm 0^b$ | $13 \pm 0^a$ | $13 \pm 1^{a,b}$ | $13 \pm 0^b$ |
| Timed up-and-go (s)[1] | $7.07 \pm 0.25^a$ | $6.89 \pm 0.26^a$ | $6.44 \pm 0.19^b$ | $7.61 \pm 0.33^a$ | $6.99 \pm 0.26^a$ | $6.80 \pm 0.32^b$ |
| 6 min walk (m)[1] | $576 \pm 14^a$ | $585 \pm 15^a$ | $616 \pm 19^b$ | $593 \pm 17^a$ | $621 \pm 16^a$ | $639 \pm 23^b$ |
| Grip strength (kg)[2] | $188 \pm 7$ | $193 \pm 6$ | $185 \pm 7$ | $185 \pm 6$ | $185 \pm 6$ | $185 \pm 6$ |

Values are mean ± SEM.
[1]Main effect for time ($P < 0.05$).
[2]Sum of left and right grip strength.
For each outcome, different letters represent significant differences within each group.
Significance accepted as $P < 0.05$.
SUPP, multi-nutrient composition group; CON, control group

TABLE 8

Aerobic fitness ($VO_2$peak test) measurements

| | SUPP | | | CON | | |
|---|---|---|---|---|---|---|
| | Baseline | 6 wk | 19 wk | Baseline | 6 wk | 19 wk |
| Relative $VO_{2Peak}$ (mL/kg/min)[1] | $23.8 \pm 0.8^a$ | $24.6 \pm 0.9^a$ | $26.2 \pm 1.2^b$ | $24.4 \pm 0.9^a$ | $24.4 \pm 1.1^a$ | $26.4 \pm 1.4^b$ |
| Absolute $VO_{2Peak}$ (L/min) | $2.0 \pm 0.1^a$ | $2.1 \pm 0.1^a$ | $2.1 \pm 0.1^b$ | $2.1 \pm 0.1^a$ | $2.1 \pm 0.1^a$ | $2.3 \pm 0.1^b$ |
| Peak power (W)[1] | $154 \pm 5^a$ | $157 \pm 5^a$ | $164 \pm 7^b$ | $158 \pm 7^a$ | $158 \pm 7^a$ | $178 \pm 10^b$ |
| Resting HR (bpm) | $78 \pm 3$ | $80 \pm 3$ | $84 \pm 3$ | $76 \pm 2$ | $81 \pm 3$ | $79 \pm 3$ |
| Maximal HR (bpm) | $143 \pm 4$ | $148 \pm 4$ | $150 \pm 4$ | $141 \pm 4$ | $141 \pm 4$ | $142 \pm 4$ |
| RER at $VO_{2peak}$ | $1.09 \pm 0.02$ | $1.08 \pm 0.01$ | $1.07 \pm 0.02$ | $1.08 \pm 0.01$ | $1.08 \pm 0.01$ | $1.07 \pm 0.02$ |

Values are mean ± SEM.
[1]Main effect for time ($P < 0.001$).
For each outcome, different letters represent significant differences within each group.
Significance accepted as $P < 0.05$.
$VO_2$peak, peak oxygen consumption; SUPP, multi-nutrient composition group; CON, control group; HR, heart rate; RER, respiratory exchange ratio glucose tolerance is improved by administration of the multi-nutrient composition in conjunction with exercise in healthy individuals.

Dietary Intake

Baseline dietary intake was not significantly different between the SUPP and CON groups, based on 3-day dietary

TABLE 9

Fasting blood lipids and insulin sensitivity indices

| | SUPP | | | CON | | |
|---|---|---|---|---|---|---|
| | Baseline | 6 wk | 19 wk | Baseline | 6 wk | 19 wk |
| Blood lipids Cholesterol (mM) | | | | | | |
| Total[1] | $4.69 \pm 0.22^a$ | $4.34 \pm 0.23^b$ | $4.56 \pm 0.30^{a,b}$ | $4.83 \pm 0.19^{a,b}$ | $4.86 \pm 0.19^a$ | $4.73 \pm 0.19^b$ |
| LDL | $2.74 \pm 0.21$ | $2.63 \pm 0.19$ | $2.77 \pm 0.25$ | $2.87 \pm 0.18$ | $2.87 \pm 0.20$ | $2.85 \pm 0.19$ |
| HDL | $1.27 \pm 0.06$ | $1.27 \pm 0.08$ | $1.28 \pm 0.09$ | $1.29 \pm 0.06$ | $1.29 \pm 0.06$ | $1.26 \pm 0.07$ |
| TAG (mM)[1] | $1.49 \pm 0.19^a$ | $0.97 \pm 0.09^{b*}$ | $1.10 \pm 0.14^b$ | $1.50 \pm 0.21^a$ | $1.52 \pm 0.18^a$ | $1.35 \pm 0.16^a$ |
| AUC | | | | | | |
| Glucose (mM · 120 min)[2] | $915 \pm 16^a$ | $890 \pm 10^a$ | $842 \pm 14^b$ | $886 \pm 11^a$ | $899 \pm 12^a$ | $869 \pm 13^b$ |
| Insulin (IU · 120 min)[2] | $4080 \pm 65^a$ | $3950 \pm 77^a$ | $3533 \pm 62^b$ | $4060 \pm 69^a$ | $3951 \pm 92^a$ | $3397 \pm 68^b$ |
| Insulin sensitivity indices | | | | | | |
| HOMA-IR[2] | $2.1 \pm 0.1^a$ | $2.1 \pm 0.1^a$ | $1.7 \pm 0.1^b$ | $2.2 \pm 0.1^a$ | $2.0 \pm 0.1^a$ | $1.7 \pm 0.1^b$ |
| OGIS | $450 \pm 9$ | $473 \pm 12$ | $468 \pm 18$ | $462 \pm 10$ | $463 \pm 13$ | $453 \pm 12$ |
| Matsuda index[2] | $5.1 \pm 0.7^a$ | $5.3 \pm 0.6^a$ | $6.4 \pm 0.8^b$ | $5.1 \pm 0.6^a$ | $5.4 \pm 0.8^a$ | $6.4 \pm 0.8^b$ |

Values are mean ± SEM.
[1]Group x time interaction (P < 0.05).
[2]Main effect for time (P < 0.01).
For each outcome, different letters represent significant differences within each group.
*Represents a significant difference from CON at that timepoint.
Significance accepted as P < 0.05.
SUPP, multi-nutrient composition group; CON, control group; TAG, triacylglyceride; OGIS, oral glucose tolerance test-based index of insulin sensitivity Fasting Lipids Fasting blood triglycerides and blood cholesterol were not significantly different between the SUPP and CON groups at baseline (Table 9). Significant group x time interactions were observed for fasting blood triglycerides (P<0.05) and blood cholesterol (P<0.05), so each group was analyzed separately for these measures. In the SUPP group, fasting blood triglycerides (−35%; P<0.01) and blood cholesterol (−7%; P<0.01) were reduced following Phase 1 and no further change was observed as a result of Phase 2. On the other hand, the CON group experienced no changes of fasting triglyceride levels throughout the study, and only experienced a decrease in fasting blood cholesterol (−3%; P<0.05) following the exercise regime of Phase 2. These findings clearly show that the administration of the multi-nutrient composition improved blood triglyceride levels and blood cholesterol levels in healthy individuals.

intake records (Table 10). Significant group x time interactions were observed for protein intake (expressed as g, g/kg body mass, and % energy; P<0.001), vitamin D (P<0.001), calcium (P<0.001), and n-3 fatty acids (P<0.01). As such, both groups were analyzed separately for those measures. In the SUPP group, participants reported a significantly increased daily protein intake (+0.6 g/kg body mass; +7% energy %) following Phase 1. Self-reported daily protein intake remained elevated compared to baseline during Phase 2. Furthermore, a significant increase in vitamin D (P<0.05), calcium (P<0.05), and n-3 fatty acids (P<0.05) intake was observed as a result of Phase 1 in the SUPP group, which remained elevated throughout Phase 2. In the CON group, no other significant changes in macronutrient or micronutrient intake were observed over the course of the intervention.

TABLE 10

Daily habitual dietary intake (including supplements) and habitual physical activity over the course of the study

| | SUPP | | | CON | | |
|---|---|---|---|---|---|---|
| | Baseline | 6 wk | 19 wk | Baseline | 6 wk | 19 wk |
| Dietary intakes | | | | | | |
| Energy (kJ)[2] | $8979 \pm 427^a$ | $10,063 \pm 674^b$ | $8782 \pm 699^{a,b}$ | $9774 \pm 481^a$ | $10,632 \pm 540^b$ | $10,113 \pm 745^{a,b}$ |

TABLE 10-continued

Daily habitual dietary intake (including supplements) and habitual physical activity over the course of the study

| | SUPP | | | CON | | |
|---|---|---|---|---|---|---|
| | Baseline | 6 wk | 19 wk | Baseline | 6 wk | 19 wk |
| Protein | | | | | | |
| g[1] | 89 ± 5$^a$ | 142 ± 8$^{b*}$ | 130 ± 7$^{b*}$ | 97 ± 6$^a$ | 100 ± 8$^a$ | 99 ± 10$^a$ |
| g/kg[1] | 1.1 ± 0.1$^a$ | 1.7 ± 0.1$^{b*}$ | 1.6 ± 0.1$^{b*}$ | 1.2 ± 0.1$^a$ | 1.2 ± 0.1$^a$ | 1.2 ± 0.1$^a$ |
| %[1] | 17 ± 1$^a$ | 24 ± 1$^{b*}$ | 26 ± 1$^{b*}$ | 17 ± 1$^a$ | 16 ± 1$^a$ | 17 ± 1$^a$ |
| Carbohydrate | | | | | | |
| G | 265 ± 14 | 257 ± 20 | 223 ± 16 | 272 ± 21 | 309 ± 21 | 304 ± 29 |
| %[1] | 50 ± 1$^a$ | 43 ± 1$^{b*}$ | 43 ± 2$^{b*}$ | 46 ± 3$^a$ | 49 ± 2$^a$ | 51 ± 3$^a$ |
| Fat | | | | | | |
| G | 71 ± 5 | 82 ± 8 | 68 ± 8 | 86 ± 6 | 89 ± 8 | 80 ± 8 |
| % | 30 ± 1 | 30 ± 1 | 28 ± 2 | 33 ± 2 | 31 ± 2 | 29 ± 2 |
| Alcohol | | | | | | |
| G | 13 ± 3 | 10 ± 2 | 11 ± 3 | 13 ± 3 | 15 ± 4 | 13 ± 4 |
| % | 4 ± 1 | 3 ± 1 | 3 ± 1 | 4 ± 1 | 4 ± 1 | 3 ± 1 |
| Vitamin D (IU)[1] | 161 ± 27$^a$ | 1061 ± 50$^{b*}$ | 1086 ± 43$^{b*}$ | 175 ± 29$^a$ | 193 ± 45$^a$ | 148 ± 40$^a$ |
| Calcium (mg)[1] | 775 ± 74$^a$ | 1491 ± 142$^{b*}$ | 1423 ± 79$^{b*}$ | 944 ± 115$^a$ | 919 ± 113$^a$ | 856 ± 118$^a$ |
| n-3 PUFA (g)[1] | 1.2 ± 0.3$^a$ | 2.5 ± 0.3$^{b*}$ | 2.3 ± 0.2$^{b*}$ | 0.9 ± 0.1$^a$ | 1.2 ± 0.2$^a$ | 1.1 ± 0.3$^a$ |
| Physical activity | | | | | | |
| AEE (kJ) | 1648 ± 343 | 1582 ± 293 | 1356 ± 297 | 1565 ± 423 | 1774 ± 481 | 1226 ± 439 |
| Average METs | 1.3 ± 0.0 | 1.4 ± 0.1 | 1.4 ± 0.0 | 1.2 ± 0.1 | 1.3 ± 0.1 | 1.3 ± 0.1 |

Values are mean ± SEM.
[1]Group x time interaction (P < 0.001).
[2]Main effect for time (P < 0.01).
For each outcome, different letters represent significant differences within each group.
*Represents a significant difference from CON at that timepoint.
Significance accepted as P < 0.05.
SUPP, multi-nutrient composition group; CON, control group; TEE, total energy expenditure; AEE, active energy expenditure; METs, metabolic equivalents A significant main effect of time was observed for daily energy intake (P<0.01). Total energy intake was significantly higher at week 6 compared to baseline (SUPP: +12%; CON: +9%, P<0.01), with no further change at week 19 (i.e. following Phase 2). Dietary fat intake and alcohol consumption did not change significantly over the course of the study.

Habitual Physical Activity

Accelerometry-based measurements of habitual physical activity (TEE, AEE, and average METs) were not different between the SUPP and CON groups at baseline (Table 8). A main effect of time was observed for TEE (P<0.01): following Phase 1, TEE did not differ from baseline. AEE and average METs did not change over the course of the study.

Collectively, the findings from this placebo controlled, double blinded clinical study surprisingly reveal that the administration of the multi-nutrient composition to an individual, or to an individual performing regular exercise, is an effective strategy for improving the lean mass, muscle strength, cognition, systemic inflammation levels, blood cholesterol levels, blood triglyceride levels and glucose tolerance of an individual.

The present compositions and methods advantageously provide individuals with one or more health benefits associated with exercise, with or without performing exercise. In addition, the present multi-nutrient composition has been scientifically validated and permits use by individuals without the expenditure of time to determine how to supplement diet, and which nutrients will provide a desired beneficial effect. The present method and composition also provides health benefits to an individual in need thereof that are synergistic with the health benefits obtained from exercise.

The invention claimed is:

1. A kit consisting of a first composition consisting of 10-70 g of a protein, 1-5 g of creatine, 500-3000 IU of vitamin D, 100-1000 mg calcium and optionally at least one physiologically acceptable excipient, and a second composition consisting of 100-1500 mg of DHA, 100-1500 mg of EPA and optionally at least one physiologically acceptable excipient, wherein the at least one physiological acceptable excipient in the first composition and the at least one physiological acceptable excipient in the second composition is selected from the group consisting of: flavouring agents, sweetening agents, anti-caking agents, flowing agents, emulsifiers, stabilizers, masking agents, colorants, preservatives, disintegrants, binders, thickeners, pH adjusters, carbohydrate and oil, and wherein the kit is useful to increase cognitive ability in an individual by about 0.5-50% and the first and second compositions are packaged separately.

2. The kit of claim 1, wherein the first composition is in powder form and the second composition is an oil.

3. The kit of claim 1, wherein the protein of the first composition is a whey protein.

4. The kit of claim 3, wherein the whey protein is a whey protein isolate, whey protein concentrate or hydrolyzed whey protein.

5. The kit of claim 1, wherein the creatine is selected from the group consisting of creatine monohydrate, creatine anhydrous, creatine citrate, creatine ethyl ester, creatine nitrate, creatine magnesium chelate, creatine hydrochloride, creatine malate, creatine pyruvate, creatine phosphate, creatine citrate malate, creatine tartrate, creatine HMB (β-hydroxy β-methylbutyrate), effervescent creatine, creatine titrate, buffered creatine, micronized creatine and any combination thereof.

6. The kit of claim 5, wherein the creatine is creatine monohydrate.

7. The kit of claim 1, wherein the vitamin D is vitamin D2, vitamin D3 or a combination thereof.

8. The kit of claim 7, wherein the vitamin D is vitamin D3.

9. The kit of claim 1, wherein the calcium is calcium carbonate.

10. The kit of claim 3, wherein the first composition comprises 15-35 g of whey protein.

11. A method of increasing cognition in an individual, comprising administering to the individual a first composition from a kit as defined in claim 1, and a second composition from a kit as defined in claim 1.

12. The method of claim 11, wherein the first and second compositions of the kit are administered to an individual performing regular exercise.

13. The kit of claim 1, wherein the kit is additionally useful to increase at least one of muscle strength or lean mass in the individual.

14. The method of claim 11, which additionally increases at least one of muscle strength or lean mass in the individual.

* * * * *